(12) United States Patent
Yang et al.

(10) Patent No.: US 11,866,489 B2
(45) Date of Patent: Jan. 9, 2024

(54) INHIBITION OF SCUBE2, A NOVEL VEGFR2 CO-RECEPTOR, SUPPRESSES TUMOR ANGIOGENESIS

(71) Applicant: Academia Sinica, Taipei (TW)

(72) Inventors: Ruey-Bing Yang, Taipei (TW); Yuh-Charn Lin, Taichung (TW)

(73) Assignee: ACADEMIA SINICA, Taipei (TW)

( * ) Notice: Subject to any disclaimer, the term of this patent is extended or adjusted under 35 U.S.C. 154(b) by 284 days.

(21) Appl. No.: 17/342,514

(22) Filed: Jun. 8, 2021

(65) Prior Publication Data

US 2021/0292401 A1 Sep. 23, 2021

Related U.S. Application Data

(62) Division of application No. 16/091,164, filed as application No. PCT/US2017/026855 on Apr. 10, 2017, now Pat. No. 11,066,466.

(60) Provisional application No. 62/322,626, filed on Apr. 14, 2016.

(51) Int. Cl.
| | | |
|---|---|---|
| *C07K 16/22* | (2006.01) | |
| *A61K 39/395* | (2006.01) | |
| *C07K 16/18* | (2006.01) | |
| *A61P 35/00* | (2006.01) | |
| *A61K 39/00* | (2006.01) | |

(52) U.S. Cl.
CPC ............ *C07K 16/22* (2013.01); *A61K 39/395* (2013.01); *A61P 35/00* (2018.01); *C07K 16/18* (2013.01); *A61K 2039/505* (2013.01); *A61K 2039/507* (2013.01); *C07K 2317/24* (2013.01); *C07K 2317/34* (2013.01); *C07K 2317/73* (2013.01); *C07K 2317/76* (2013.01)

(58) Field of Classification Search
CPC ................ C07K 2317/24; C07K 16/22; A61K 2039/507; A61P 35/00
See application file for complete search history.

(56) References Cited

U.S. PATENT DOCUMENTS

2009/0264361 A1* 10/2009 Yang ...................... C07K 14/47
435/7.1

* cited by examiner

*Primary Examiner* — Ruixiang Li
(74) *Attorney, Agent, or Firm* — Hsiu-Ming Saunders; INTELLECTUAL PROPERTY CONNECTIONS INC.

(57) ABSTRACT

An isolated anti-SCUBE2 antibody or a binding fragment thereof is disclosed. The anti-SCUBE2 antibody comprises an antigen binding region that specifically binds to a target domain located within SCUBE2 (SEQ ID NO: 66) and exhibits a property of inhibiting VEGF-induced angiogenesis. The target domain is selected from the group consisting of the EGF-like motifs 4 to 6 ranging from a.a. position 175 to 323, or the spacer region ranging from a.a. position 441 to 659, or the first cys-rich motif ranging from a.a. position 668 to 725 of SCUBE2 (SEQ ID NO: 66). The anti-SCUBE2 antibody or binding fragment thereof is for use in treating a disease associated with VEGF-induced angiogenesis, or for use in treating a tumor or inhibiting tumor angiogenesis and cancer cell growth in a subject in need thereof.

17 Claims, 16 Drawing Sheets

Specification includes a Sequence Listing.

A B16F10 melanoma cells

B LLC lung carcinoma cells

C B16F10 melanoma cells

D LLC lung carcinoma cells

E B16F10 melanoma cells

F LLC lung carcinoma cells

G

H

A

B

| Anti-SCUBE2 mAb | | | Specificity by Western blotting | | | | | Anti-angiogenetic effect |
|---|---|---|---|---|---|---|---|---|
| Name | Isotype | Targeting sequences | hSCUBE1 | hSCUBE2 | hSCUBE3 | mSCUBE2 | zSCUBE2 | |
| EGF-C3 | IgG2a | a.a. 175-323 | - | + | - | - | - | ++ |
| SP-A1 | IgG1 | a.a. 441-659 | - | + | - | + | - | + |
| SP-B1 | IgG1 | a.a. 441-659 | - | + | - | + | - | ++ |
| SP-B2 | IgG1 | a.a. 441-659 | - | + | - | - | - | ++ |
| CR-#5 | IgG2b | a.a. 668-725 | - | + | - | + | - | ++ |

SEQUENCE LISTING

<160> NUMBER OF SEQ ID NOS: 102

<210> SEQ ID NO 1
<211> LENGTH: 119
<212> TYPE: PRT
<213> ORGANISM: Artificial Sequence

```
<220> FEATURE:
<223> OTHER INFORMATION: mAb EGF-C3 VH  domain

<400> SEQUENCE: 1

Glu Val Lys Leu Val Glu Ser Gly Gly Gly Leu Val Gln Pro Gly Gly
1               5                   10                  15

Ser Arg Lys Leu Ser Cys Val Ala Ser Gly Phe Thr Ile Ser Ser Phe
                20                  25                  30

Gly Met His Trp Val Arg Gln Ala Pro Glu Arg Gly Leu Glu Trp Val
            35                  40                  45

Ala Tyr Ile Ser Ser Gly Ser Asn Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Trp Ser Glu Asp Thr Ala Met Tyr Tyr Cys
                85                  90                  95

Ala Arg Ser Gly Thr Leu Asp Gly Trp Phe Thr Tyr Trp Gly Arg Gly
            100                 105                 110

Thr Leu Val Thr Val Ser Thr
        115

<210> SEQ ID NO 2
<211> LENGTH: 112
<212> TYPE: PRT
<213> ORGANISM: Artificial Sequence
<220> FEATURE:
<223> OTHER INFORMATION: mAb EGF-C3 VL domain

<400> SEQUENCE: 2

Asp Ile Val Met Thr Gln Pro Pro Leu Ser Leu Pro Val Ser Leu Gly
1               5                   10                  15

Asp Gln Ala Ser Ile Ser Cys Arg Ser Ser Gln Ser Ile Leu His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Leu Phe Asn Arg Phe Ser Gly Val Pro
    50                  55                  60

Asp Arg Phe Asn Gly Ser Gly Ser Gly Thr Asp Phe Thr Leu Lys Ile
65                  70                  75                  80

Ser Arg Ala Glu Ala Glu Asp Leu Gly Val Tyr Tyr Cys Leu Gln Gly
                85                  90                  95

Ser His Val Pro Pro Thr Phe Gly Ala Gly Thr Lys Leu Glu Ile Lys
            100                 105                 110

<210> SEQ ID NO 3
<211> LENGTH: 10
<212> TYPE: PRT
<213> ORGANISM: Artificial Sequence
<220> FEATURE:
<223> OTHER INFORMATION: mAb EGF-C3 VH  CDR1

<400> SEQUENCE: 3

Gly Phe Thr Ile Ser Ser Phe Gly Met His
1               5                   10

<210> SEQ ID NO 4
<211> LENGTH: 17
<212> TYPE: PRT
<213> ORGANISM: Artificial Sequence
<220> FEATURE:
```

-continued

<223> OTHER INFORMATION: mAb EGF-C3 VH CDR2

<400> SEQUENCE: 4

```
Tyr Ile Ser Ser Gly Ser Asn Thr Ile Tyr Tyr Ala Asp Thr Val Lys
1               5                   10                  15
Gly
```

<210> SEQ ID NO 5
<211> LENGTH: 10
<212> TYPE: PRT
<213> ORGANISM: Artificial Sequence
<220> FEATURE:
<223> OTHER INFORMATION: mAb EGF-C3 VH CDR3

<400> SEQUENCE: 5

```
Ser Gly Thr Leu Asp Gly Trp Phe Thr Tyr
1               5                   10
```

<210> SEQ ID NO 6
<211> LENGTH: 16
<212> TYPE: PRT
<213> ORGANISM: Artificial Sequence
<220> FEATURE:
<223> OTHER INFORMATION: mAb EGF-C3 VL CDR1

<400> SEQUENCE: 6

```
Arg Ser Ser Gln Ser Ile Leu His Ser Asn Gly Asn Thr Tyr Leu Glu
1               5                   10                  15
```

<210> SEQ ID NO 7
<211> LENGTH: 7
<212> TYPE: PRT
<213> ORGANISM: Artificial Sequence
<220> FEATURE:
<223> OTHER INFORMATION: mAb EGF-C3 VL CDR2

<400> SEQUENCE: 7

```
Lys Leu Phe Asn Arg Phe Ser
1               5
```

<210> SEQ ID NO 8
<211> LENGTH: 9
<212> TYPE: PRT
<213> ORGANISM: Artificial Sequence
<220> FEATURE:
<223> OTHER INFORMATION: mAb EGF-C3 VL CDR3

<400> SEQUENCE: 8

```
Leu Gln Gly Ser His Val Pro Pro Thr
1               5
```

<210> SEQ ID NO 9
<211> LENGTH: 25
<212> TYPE: PRT
<213> ORGANISM: Artificial Sequence
<220> FEATURE:
<223> OTHER INFORMATION: mAb EGF-C3 VH FW1

<400> SEQUENCE: 9

```
Glu Val Lys Leu Val Glu Ser Gly Gly Gly Leu Val Gln Pro Gly Gly
1               5                   10                  15
Ser Arg Lys Leu Ser Cys Val Ala Ser
            20                  25
```

<210> SEQ ID NO 10

```
<211> LENGTH: 14
<212> TYPE: PRT
<213> ORGANISM: Artificial Sequence
<220> FEATURE:
<223> OTHER INFORMATION: mAb EGF-C3 VH FW2

<400> SEQUENCE: 10

Trp Val Arg Gln Ala Pro Glu Arg Gly Leu Glu Trp Val Ala
1               5                   10

<210> SEQ ID NO 11
<211> LENGTH: 32
<212> TYPE: PRT
<213> ORGANISM: Artificial Sequence
<220> FEATURE:
<223> OTHER INFORMATION: mAb EGF-C3 VH FW3

<400> SEQUENCE: 11

Arg Phe Thr Ile Ser Arg Asp Asn Pro Lys Asn Thr Leu Phe Leu Gln
1               5                   10                  15

Met Thr Ser Leu Trp Ser Glu Asp Thr Ala Met Tyr Tyr Cys Ala Arg
            20                  25                  30

<210> SEQ ID NO 12
<211> LENGTH: 11
<212> TYPE: PRT
<213> ORGANISM: Artificial Sequence
<220> FEATURE:
<223> OTHER INFORMATION: mAb EGF-C3 VH  FW4

<400> SEQUENCE: 12

Trp Gly Arg Gly Thr Leu Val Thr Val Ser Thr
1               5                   10

<210> SEQ ID NO 13
<211> LENGTH: 23
<212> TYPE: PRT
<213> ORGANISM: Artificial Sequence
<220> FEATURE:
<223> OTHER INFORMATION: mAb EGF-C3 VL  FW1

<400> SEQUENCE: 13

Asp Ile Val Met Thr Gln Pro Pro Leu Ser Leu Pro Val Ser Leu Gly
1               5                   10                  15

Asp Gln Ala Ser Ile Ser Cys
            20

<210> SEQ ID NO 14
<211> LENGTH: 15
<212> TYPE: PRT
<213> ORGANISM: Artificial Sequence
<220> FEATURE:
<223> OTHER INFORMATION: mAb EGF-C3 VL FW2

<400> SEQUENCE: 14

Trp Tyr Leu Gln Lys Pro Gly Gln Ser Pro Lys Leu Leu Ile Tyr
1               5                   10                  15

<210> SEQ ID NO 15
<211> LENGTH: 32
<212> TYPE: PRT
<213> ORGANISM: Artificial Sequence
<220> FEATURE:
<223> OTHER INFORMATION: mAb EGF-C3 VL  FW3

<400> SEQUENCE: 15
```

```
Gly Val Pro Asp Arg Phe Asn Gly Ser Gly Ser Gly Thr Asp Phe Thr
1               5                   10                  15

Leu Lys Ile Ser Arg Ala Glu Ala Glu Asp Leu Gly Val Tyr Tyr Cys
            20                  25                  30
```

<210> SEQ ID NO 16
<211> LENGTH: 10
<212> TYPE: PRT
<213> ORGANISM: Artificial Sequence
<220> FEATURE:
<223> OTHER INFORMATION: mAb EGF-C3 VL FW4

<400> SEQUENCE: 16

```
Phe Gly Ala Gly Thr Lys Leu Glu Ile Lys
1               5                   10
```

<210> SEQ ID NO 17
<211> LENGTH: 119
<212> TYPE: PRT
<213> ORGANISM: Artificial Sequence
<220> FEATURE:
<223> OTHER INFORMATION: mAb SP-A1 /B1 VH domain

<400> SEQUENCE: 17

```
Glu Val Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Asp Thr Asn Asn Asn Gln Lys Phe
    50                  55                  60

Lys Gly Lys Ala Thr Leu Thr Val Asp Lys Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Ser Tyr Arg Tyr Leu Ala Trp Phe Ala Tyr Trp Gly Gln Gly
                100                 105                 110

Thr Leu Val Thr Val Ser Ala
            115
```

<210> SEQ ID NO 18
<211> LENGTH: 112
<212> TYPE: PRT
<213> ORGANISM: Artificial Sequence
<220> FEATURE:
<223> OTHER INFORMATION: mAb SP-A1 /B1 VL domain

<400> SEQUENCE: 18

```
Asp Ile Val Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
```

85                  90                  95
Ser His Ile Pro Tyr Thr Phe Gly Gly Gly Thr Lys Leu Glu Leu Lys
                100                 105                 110

<210> SEQ ID NO 19
<211> LENGTH: 10
<212> TYPE: PRT
<213> ORGANISM: Artificial Sequence
<220> FEATURE:
<223> OTHER INFORMATION: mAb SP-A1/B1 VH CDR1

<400> SEQUENCE: 19

Gly Tyr Ala Phe Thr Ser Tyr Asn Met Tyr
1               5                   10

<210> SEQ ID NO 20
<211> LENGTH: 17
<212> TYPE: PRT
<213> ORGANISM: Artificial Sequence
<220> FEATURE:
<223> OTHER INFORMATION: mAb SP-A1/B1 VH CDR2

<400> SEQUENCE: 20

Tyr Ile Asp Pro Tyr Asn Gly Asp Thr Asn Asn Asn Gln Lys Phe Lys
1               5                   10                  15
Gly

<210> SEQ ID NO 21
<211> LENGTH: 10
<212> TYPE: PRT
<213> ORGANISM: Artificial Sequence
<220> FEATURE:
<223> OTHER INFORMATION: mAb SP-A1/B1 VH CDR3

<400> SEQUENCE: 21

Ser Tyr Arg Tyr Leu Ala Trp Phe Ala Tyr
1               5                   10

<210> SEQ ID NO 22
<211> LENGTH: 16
<212> TYPE: PRT
<213> ORGANISM: Artificial Sequence
<220> FEATURE:
<223> OTHER INFORMATION: mAb SP-A1/B1VL CDR1

<400> SEQUENCE: 22

Arg Ser Ser Gln Ser Ile Val His Ser Asn Gly Asn Thr Tyr Leu Glu
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: mAb SP-A1/B1 VL CDR2

<400> SEQUENCE: 23

Thr Val Ser Asn Arg Phe Ser
1               5

<210> SEQ ID NO 24
<211> LENGTH: 9
<212> TYPE: PRT
<213> ORGANISM: Artificial Sequence
<220> FEATURE:
<223> OTHER INFORMATION: mAb SP-A1/B1 VL CDR3

-continued

```
<400> SEQUENCE: 24

Phe Gln Gly Ser His Ile Pro Tyr Thr
1               5

<210> SEQ ID NO 25
<211> LENGTH: 25
<212> TYPE: PRT
<213> ORGANISM: Artificial Sequence
<220> FEATURE:
<223> OTHER INFORMATION: mAb SP-A1/B1 VH  FW1

<400> SEQUENCE: 25

Glu Val Gln Leu Gln Gln Ser Gly Pro Glu Leu Val Lys Pro Gly Ala
1               5                   10                  15

Ser Val Lys Val Ser Cys Lys Ala Ser
            20                  25

<210> SEQ ID NO 26
<211> LENGTH: 14
<212> TYPE: PRT
<213> ORGANISM: Artificial Sequence
<220> FEATURE:
<223> OTHER INFORMATION: mAb SP-A1/B1 VH  FW2

<400> SEQUENCE: 26

Trp Val Lys Gln Ser His Gly Lys Ser Leu Glu Trp Ile Gly
1               5                   10

<210> SEQ ID NO 27
<211> LENGTH: 32
<212> TYPE: PRT
<213> ORGANISM: Artificial Sequence
<220> FEATURE:
<223> OTHER INFORMATION: mAb SP-A1/B1 VH  FW3

<400> SEQUENCE: 27

Lys Ala Thr Leu Thr Val Asp Lys Ser Ser Ser Thr Ala Tyr Met His
1               5                   10                  15

Leu Asn Ser Leu Thr Ser Glu Asp Ser Ala Val Tyr Tyr Cys Ala Arg
            20                  25                  30

<210> SEQ ID NO 28
<211> LENGTH: 11
<212> TYPE: PRT
<213> ORGANISM: Artificial Sequence
<220> FEATURE:
<223> OTHER INFORMATION: mAb SP-A1/B1 VH  FW4

<400> SEQUENCE: 28

Trp Gly Gln Gly Thr Leu Val Thr Val Ser Ala
1               5                   10

<210> SEQ ID NO 29
<211> LENGTH: 23
<212> TYPE: PRT
<213> ORGANISM: Artificial Sequence
<220> FEATURE:
<223> OTHER INFORMATION: mAb SP-A1/B1 VL  FW1

<400> SEQUENCE: 29

Asp Ile Val Met Thr Gln Ser Pro Leu Ser Leu Pro Val Ser Leu Gly
1               5                   10                  15

Asp Gln Ala Ser Ile Ser Cys
            20
```

<210> SEQ ID NO 30
<211> LENGTH: 15
<212> TYPE: PRT
<213> ORGANISM: Artificial Sequence
<220> FEATURE:
<223> OTHER INFORMATION: mAb SP-A1/B1 VL FW2

<400> SEQUENCE: 30

Trp Tyr Leu Gln Lys Pro Gly Gln Ser Pro Lys Leu Leu Ile Tyr
1               5                   10                  15

<210> SEQ ID NO 31
<211> LENGTH: 32
<212> TYPE: PRT
<213> ORGANISM: Artificial Sequence
<220> FEATURE:
<223> OTHER INFORMATION: mAb SP-A1/B1 VL FW3

<400> SEQUENCE: 31

Gly Val Pro Asp Arg Phe Ser Gly Ser Gly Ser Gly Thr Asp Phe Thr
1               5                   10                  15

Leu Arg Ile Ser Arg Val Glu Ala Glu Asp Leu Gly Val Tyr Tyr Cys
            20                  25                  30

<210> SEQ ID NO 32
<211> LENGTH: 10
<212> TYPE: PRT
<213> ORGANISM: Artificial Sequence
<220> FEATURE:
<223> OTHER INFORMATION: mAb SP-A1/B1 VL FW4

<400> SEQUENCE: 32

Phe Gly Gly Gly Thr Lys Leu Glu Leu Lys
1               5                   10

<210> SEQ ID NO 33
<211> LENGTH: 122
<212> TYPE: PRT
<213> ORGANISM: Artificial Sequence
<220> FEATURE:
<223> OTHER INFORMATION: mAb SP-B2 VH domain

<400> SEQUENCE: 33

Glu Val Gln Arg Val Glu Ser Gly Gly Gly Leu Val Lys Pro Gly Gly
1               5                   10                  15

Ser Leu Lys Leu Ser Cys Ala Ala Ser Gly Phe Thr Phe Arg Asn Tyr
            20                  25                  30

Ala Met Ser Trp Val Arg Gln Thr Thr Glu Lys Lys Leu Glu Trp Val
        35                  40                  45

Ala Thr Ile Asn Asp Val Gly Ser Tyr Thr Tyr Phe Pro Ala Ser Val
    50                  55                  60

Lys Gly Arg Phe Thr Val Ser Arg Asp Asn Thr Lys Asn Thr Leu Tyr
65                  70                  75                  80

Leu Gln Met Ser Ser Leu Arg Ser Glu Asp Thr Ala Met Tyr Tyr Cys
                85                  90                  95

Val Thr Ser Ser Asp Thr Val Pro His His Ala Leu Asp Tyr Trp
            100                 105                 110

Gly Gln Gly Ser Ser Val Thr Val Ser Ser
        115                 120

<210> SEQ ID NO 34

```
<211> LENGTH: 110
<212> TYPE: PRT
<213> ORGANISM: Artificial Sequence
<220> FEATURE:
<223> OTHER INFORMATION: mAb SP-B2 VL domain

<400> SEQUENCE: 34

Asp Ile Val Met Thr Gln Pro Pro Ala Ser Leu Ala Val Ser Leu Gly
1               5                  10                  15

Gln Arg Ala Thr Val Phe Cys Arg Ala Ser Gln Asn Val Asp Ser Arg
            20                  25                  30

Gly Ile Ser Phe Met His Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Arg Gly Ser Gly Ser Gly Thr Asp Phe Thr Leu Asn Ile His
65                  70                  75                  80

Pro Val Glu Glu Glu Asp Val Ala Thr Tyr Tyr Cys Gln Gln Ser Val
                85                  90                  95

Glu Asp Leu Thr Phe Gly Gly Gly Thr Lys Leu Glu Leu Lys
            100                 105                 110

<210> SEQ ID NO 35
<211> LENGTH: 10
<212> TYPE: PRT
<213> ORGANISM: Artificial Sequence
<220> FEATURE:
<223> OTHER INFORMATION: mAb SP-B2 VH CDR1

<400> SEQUENCE: 35

Gly Phe Thr Phe Arg Asn Tyr Ala Met Ser
1               5                  10

<210> SEQ ID NO 36
<211> LENGTH: 17
<212> TYPE: PRT
<213> ORGANISM: Artificial Sequence
<220> FEATURE:
<223> OTHER INFORMATION: mAb SP-B2 VH CDR2

<400> SEQUENCE: 36

Thr Ile Asn Asp Val Gly Ser Tyr Thr Tyr Phe Pro Ala Ser Val Lys
1               5                  10                  15

Gly

<210> SEQ ID NO 37
<211> LENGTH: 13
<212> TYPE: PRT
<213> ORGANISM: Artificial Sequence
<220> FEATURE:
<223> OTHER INFORMATION: mAb SP-B2 VH CDR3

<400> SEQUENCE: 37

Ser Ser Asp Thr Val Pro His His His Ala Leu Asp Tyr
1               5                  10

<210> SEQ ID NO 38
<211> LENGTH: 15
<212> TYPE: PRT
<213> ORGANISM: Artificial Sequence
<220> FEATURE:
<223> OTHER INFORMATION: mAb SP-B2 VL CDR1

<400> SEQUENCE: 38
```

Arg Ala Ser Gln Asn Val Asp Ser Arg Gly Ile Ser Phe Met His
1               5                   10                  15

<210> SEQ ID NO 39
<211> LENGTH: 7
<212> TYPE: PRT
<213> ORGANISM: Artificial Sequence
<220> FEATURE:
<223> OTHER INFORMATION: mAb SP-B2 VL CDR2

<400> SEQUENCE: 39

Ala Ala Ser Asn Leu Glu Ser
1               5

<210> SEQ ID NO 40
<211> LENGTH: 8
<212> TYPE: PRT
<213> ORGANISM: Artificial Sequence
<220> FEATURE:
<223> OTHER INFORMATION: mAb SP-B2 VL CDR3

<400> SEQUENCE: 40

Gln Gln Ser Val Glu Asp Leu Thr
1               5

<210> SEQ ID NO 41
<211> LENGTH: 25
<212> TYPE: PRT
<213> ORGANISM: Artificial Sequence
<220> FEATURE:
<223> OTHER INFORMATION: mAb SP-B2 VH FW1

<400> SEQUENCE: 41

Glu Val Gln Arg Val Glu Ser Gly Gly Gly Leu Val Lys Pro Gly Gly
1               5                   10                  15

Ser Leu Lys Leu Ser Cys Ala Ala Ser
            20                  25

<210> SEQ ID NO 42
<211> LENGTH: 14
<212> TYPE: PRT
<213> ORGANISM: Artificial Sequence
<220> FEATURE:
<223> OTHER INFORMATION: mAb SP-B2 VH FW2

<400> SEQUENCE: 42

Trp Val Arg Gln Thr Thr Glu Lys Lys Leu Glu Trp Val Ala
1               5                   10

<210> SEQ ID NO 43
<211> LENGTH: 32
<212> TYPE: PRT
<213> ORGANISM: Artificial Sequence
<220> FEATURE:
<223> OTHER INFORMATION: mAb SP-B2 VH FW3

<400> SEQUENCE: 43

Arg Phe Thr Val Ser Arg Asp Asn Thr Lys Asn Thr Leu Tyr Leu Gln
1               5                   10                  15

Met Ser Ser Leu Arg Ser Glu Asp Thr Ala Met Tyr Tyr Cys Val Thr
            20                  25                  30

<210> SEQ ID NO 44
<211> LENGTH: 11
<212> TYPE: PRT

```
<213> ORGANISM: Artificial Sequence
<220> FEATURE:
<223> OTHER INFORMATION: mAb SP-B2 VH  FW4

<400> SEQUENCE: 44

Trp Gly Gln Gly Ser Ser Val Thr Val Ser Ser
1               5                   10

<210> SEQ ID NO 45
<211> LENGTH: 23
<212> TYPE: PRT
<213> ORGANISM: Artificial Sequence
<220> FEATURE:
<223> OTHER INFORMATION: mAb SP-B2 VL FW1

<400> SEQUENCE: 45

Asp Ile Val Met Thr Gln Pro Pro Ala Ser Leu Ala Val Ser Leu Gly
1               5                   10                  15

Gln Arg Ala Thr Val Phe Cys
            20

<210> SEQ ID NO 46
<211> LENGTH: 15
<212> TYPE: PRT
<213> ORGANISM: Artificial Sequence
<220> FEATURE:
<223> OTHER INFORMATION: mAb SP-B2 VL FW2

<400> SEQUENCE: 46

Trp Tyr Gln Gln Lys Pro Gly Gln Pro Pro Lys Leu Leu Ile Tyr
1               5                   10                  15

<210> SEQ ID NO 47
<211> LENGTH: 32
<212> TYPE: PRT
<213> ORGANISM: Artificial Sequence
<220> FEATURE:
<223> OTHER INFORMATION: mAb SP-B2 VL  FW3

<400> SEQUENCE: 47

Gly Ile Pro Ala Arg Phe Arg Gly Ser Gly Ser Gly Thr Asp Phe Thr
1               5                   10                  15

Leu Asn Ile His Pro Val Glu Glu Glu Asp Val Ala Thr Tyr Tyr Cys
                20                  25                  30

<210> SEQ ID NO 48
<211> LENGTH: 10
<212> TYPE: PRT
<213> ORGANISM: Artificial Sequence
<220> FEATURE:
<223> OTHER INFORMATION: mAb SP-B2 VL FW4

<400> SEQUENCE: 48

Phe Gly Gly Gly Thr Lys Leu Glu Leu Lys
1               5                   10

<210> SEQ ID NO 49
<211> LENGTH: 120
<212> TYPE: PRT
<213> ORGANISM: Artificial Sequence
<220> FEATURE:
<223> OTHER INFORMATION: mAb CR-#5 VH  domain

<400> SEQUENCE: 49

Glu Val Gln Arg Val Glu Ser Gly Gly Asp Leu Val Lys Pro Gly Gly
1               5                   10                  15
```

Thr Leu Lys Leu Ser Cys Ala Ala Ser Gly Phe Thr Phe Arg Asn Tyr
            20                  25                  30

Gly Met Ser Trp Val Arg Gln Thr Pro Asp Lys Arg Leu Glu Trp Val
            35                  40                  45

Ala Thr Ile Ser Ser Gly Gly Val Tyr Ile Tyr Tyr Pro Asp Ser Val
50                      55                  60

Lys Gly Arg Phe Thr Ile Ser Arg Asp Asn Ala Lys Asn Thr Leu Phe
65                  70                  75                  80

Leu Gln Met Ser Ser Leu Arg Ser Glu Asp Ser Ala Met Tyr Tyr Cys
                85                  90                  95

Ala Arg Asp Asp Tyr Asp Gly Arg Gly Tyr Phe Asp Tyr Trp Gly Gln
            100                 105                 110

Gly Thr Thr Leu Thr Val Ser Ser
            115                 120

<210> SEQ ID NO 50
<211> LENGTH: 112
<212> TYPE: PRT
<213> ORGANISM: Artificial Sequence
<220> FEATURE:
<223> OTHER INFORMATION: mAb CR-#5 VL domain

<400> SEQUENCE: 50

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Pro Thr Phe Gly Ser Gly Thr Lys Leu Asp Ile Lys
            100                 105                 110

<210> SEQ ID NO 51
<211> LENGTH: 10
<212> TYPE: PRT
<213> ORGANISM: Artificial Sequence
<220> FEATURE:
<223> OTHER INFORMATION: mAb CR-#5 VH CDR1

<400> SEQUENCE: 51

Gly Phe Thr Phe Arg Asn Tyr Gly Met Ser
1               5                   10

<210> SEQ ID NO 52
<211> LENGTH: 17
<212> TYPE: PRT
<213> ORGANISM: Artificial Sequence
<220> FEATURE:
<223> OTHER INFORMATION: mAb CR-#5 VH CDR2

<400> SEQUENCE: 52

Thr Ile Ser Ser Gly Gly Val Tyr Ile Tyr Tyr Pro Asp Ser Val Lys
1               5                   10                  15

Gly

<210> SEQ ID NO 53
<211> LENGTH: 13
<212> TYPE: PRT
<213> ORGANISM: Artificial Sequence
<220> FEATURE:
<223> OTHER INFORMATION: mAb CR-#5 VH CDR3

<400> SEQUENCE: 53

Ala Arg Asp Asp Tyr Asp Gly Arg Gly Tyr Phe Asp Tyr
1               5                   10

<210> SEQ ID NO 54
<211> LENGTH: 17
<212> TYPE: PRT
<213> ORGANISM: Artificial Sequence
<220> FEATURE:
<223> OTHER INFORMATION: mAb CR-#5 VL CDR1

<400> SEQUENCE: 54

Lys Ser Ser Gln Ser Leu Leu Asn Ser Arg Thr Arg Lys Asn Tyr Leu
1               5                   10                  15

Ala

<210> SEQ ID NO 55
<211> LENGTH: 7
<212> TYPE: PRT
<213> ORGANISM: Artificial Sequence
<220> FEATURE:
<223> OTHER INFORMATION: mAb CR-#5 VL CDR2

<400> SEQUENCE: 55

Trp Ala Ser Thr Arg Glu Ser
1               5

<210> SEQ ID NO 56
<211> LENGTH: 8
<212> TYPE: PRT
<213> ORGANISM: Artificial Sequence
<220> FEATURE:
<223> OTHER INFORMATION: mAb CR-#5 VL CDR3

<400> SEQUENCE: 56

Lys Gln Ser Tyr Asn Leu Pro Thr
1               5

<210> SEQ ID NO 57
<211> LENGTH: 25
<212> TYPE: PRT
<213> ORGANISM: Artificial Sequence
<220> FEATURE:
<223> OTHER INFORMATION: mAb CR-#5 VH FW1

<400> SEQUENCE: 57

Glu Val Gln Arg Val Glu Ser Gly Gly Asp Leu Val Lys Pro Gly Gly
1               5                   10                  15

Thr Leu Lys Leu Ser Cys Ala Ala Ser
            20                  25

<210> SEQ ID NO 58
<211> LENGTH: 14
<212> TYPE: PRT
<213> ORGANISM: Artificial Sequence
<220> FEATURE:
<223> OTHER INFORMATION: mAb CR-#5 VH FW2

-continued

```
<400> SEQUENCE: 58

Trp Val Arg Gln Thr Pro Asp Lys Arg Leu Glu Trp Val Ala
1               5                   10

<210> SEQ ID NO 59
<211> LENGTH: 30
<212> TYPE: PRT
<213> ORGANISM: Artificial Sequence
<220> FEATURE:
<223> OTHER INFORMATION: mAb CR-#5 VH  FW3

<400> SEQUENCE: 59

Arg Phe Thr Ile Ser Arg Asp Asn Ala Lys Asn Thr Leu Phe Leu Gln
1               5                   10                  15

Met Ser Ser Leu Arg Ser Glu Asp Ser Ala Met Tyr Tyr Cys
            20                  25                  30

<210> SEQ ID NO 60
<211> LENGTH: 11
<212> TYPE: PRT
<213> ORGANISM: Artificial Sequence
<220> FEATURE:
<223> OTHER INFORMATION: mAb CR-#5 VH  FW4

<400> SEQUENCE: 60

Trp Gly Gln Gly Thr Thr Leu Thr Val Ser Ser
1               5                   10

<210> SEQ ID NO 61
<211> LENGTH: 23
<212> TYPE: PRT
<213> ORGANISM: Artificial Sequence
<220> FEATURE:
<223> OTHER INFORMATION: mAb CR-#5 VL  FW1

<400> SEQUENCE: 61

Asp Ile Val Met Ser Gln Ser Pro Ser Ser Leu Ala Val Ser Ala Gly
1               5                   10                  15

Glu Lys Val Thr Met Ser Cys
            20

<210> SEQ ID NO 62
<211> LENGTH: 15
<212> TYPE: PRT
<213> ORGANISM: Artificial Sequence
<220> FEATURE:
<223> OTHER INFORMATION: mAb CR-#5 VL  FW2

<400> SEQUENCE: 62

Trp Tyr Gln Gln Lys Pro Gly Gln Ser Pro Lys Leu Leu Ile Tyr
1               5                   10                  15

<210> SEQ ID NO 63
<211> LENGTH: 32
<212> TYPE: PRT
<213> ORGANISM: Artificial Sequence
<220> FEATURE:
<223> OTHER INFORMATION: mAb CR-#5 VL  FW3

<400> SEQUENCE: 63

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30
```

<210> SEQ ID NO 64
<211> LENGTH: 10
<212> TYPE: PRT
<213> ORGANISM: Artificial Sequence
<220> FEATURE:
<223> OTHER INFORMATION: mAb CR-#5 VL FW4

<400> SEQUENCE: 64

Phe Gly Ser Gly Thr Lys Leu Asp Ile Lys
1               5                   10

<210> SEQ ID NO 65
<211> LENGTH: 3086
<212> TYPE: DNA
<213> ORGANISM: Artificial Sequence
<220> FEATURE:
<223> OTHER INFORMATION: SCUBE2 cDNA

<400> SEQUENCE: 65

| | | | | | |
|---|---|---|---|---|---|
| atggggtcg | cgggccgcaa | ccgtcccggg | gcggcctggg | cggtgctgct | gctgctgctg | 60 |
| ctgctgccgc | cactgctgct | gctggcgggg | gccgtcccgc | cgggtcgggg | ccgtgccgcg | 120 |
| gggccgcagg | aggatgtaga | tgagtgtgcc | caagggctag | atgactgcca | tgccgacgcc | 180 |
| ctgtgtcaga | cacacccac | ctcctacaag | tgctcctgca | agcctggcta | ccaaggggaa | 240 |
| ggcaggcagt | gtgaggacat | cgatgaatgt | ggaaatgagc | tcaatggagg | ctgtgtccat | 300 |
| gactgtttga | atattccagg | caattatcgt | tgcacttgtt | ttgatggctt | catgttggct | 360 |
| catgacggtc | ataattgtct | tgatgtggac | gagtgcctgg | agaacaatgg | cggctgccag | 420 |
| catacctgtg | tcaacgtcat | ggggagctat | gagtgctgct | gcaaggaggg | gttttcctg | 480 |
| agtgacaatc | agcacacctg | cattcaccgc | tcggaagagg | gcctgagctg | catgaataag | 540 |
| gatcacggct | gtagtcacat | ctgcaaggag | gccccaaggg | gcagcgtcgc | ctgtgagtgc | 600 |
| aggcctggtt | ttgagctggc | caagaaccag | agagactgca | tcttgacctg | taaccatggg | 660 |
| aacggtgggt | gccagcactc | ctgtgacgat | acagccgatg | cccagagtg | cagctgccat | 720 |
| ccacagtaca | agatgcacac | agatgggagg | agctgccttg | agcgagagga | cactgtcctg | 780 |
| gaggtgacag | agagcaacac | cacatcagtg | gtggatgggg | ataaacgggt | gaaacggcgg | 840 |
| ctgctcatgg | aaacgtgtgc | tgtcaacaat | ggaggctgtg | accgcacctg | taaggatact | 900 |
| tcgacaggtg | tccactgcag | ttgtcctgtt | ggattcactc | tccagttgga | tgggaagaca | 960 |
| tgtaaagata | ttgatgagtg | ccagacccgc | aatggaggtt | gtgatcattt | ctgcaaaaac | 1020 |
| atcgtgggca | gttttgactg | cggctgcaag | aaaggattta | attattaac | agatgagaag | 1080 |
| tcttgccaag | atgtggatga | gtgctctttg | gataggacct | gtgaccacag | ctgcatcaac | 1140 |
| caccctggca | catttgcttg | tgcttgcaac | cgagggtaca | ccctgtatgg | cttcacccac | 1200 |
| tgtggagaca | ccaatgagtg | cagcatcaac | aacggaggct | gtcagcaggt | ctgtgtgaac | 1260 |
| acagtgggca | gctatgaatg | ccagtgccac | cctgggtaca | agctccactg | gaataaaaaa | 1320 |
| gactgtgtgg | aagtgaaggg | gctcctgccc | acaagtgtgt | caccccgtgt | gtccctgcac | 1380 |
| tgcggtaaga | gtggtggagg | agacgggtgc | ttcctcagat | gtcactctgg | cattcacctc | 1440 |
| tcttcaggac | tgcaagggc | ctactctgtc | acctgtggct | cttcctctcc | tctcaggaac | 1500 |
| aaacaacaaa | aatcaaatga | ctctgctttt | ggggatgtca | ccaccatcag | gacaagtgta | 1560 |
| acctttaagc | taaatgaagg | caagtgtagt | ttgaaaaatg | ctgagctgtt | tcccgagggt | 1620 |
| ctgcgaccag | cactaccaga | gaagcacagc | tcagtaaaag | agagcttccg | ctacgtaaac | 1680 |

-continued

```
cttacatgca gctctggcaa gcaagtccca ggagcccctg gccgaccaag cacccctaag    1740
gaaatgttta tcactgttga gtttgagctt gaaactaacc aaaaggaggt gacagcttct    1800
tgtgacctga gctgcatcgt aaagcgaacc gagaagcggc tccgtaaagc catccgcacg    1860
ctcagaaagg ccgtccacag ggagcagttt cacctccagc tctcaggcat gaacctcgac    1920
gtggctaaaa agcctcccag aacatctgaa cgccaggcag agtcctgtgg agtgggccag    1980
ggtcatgcag aaaaccaatg tgtcagttgc agggctggga cctattatga tggagcacga    2040
gaacgctgca ttttatgtcc aaatggaacc ttccaaaatg aggaaggaca aatgacttgt    2100
gaaccatgcc aagaccagg aaattctggg gccctgaaga ccccagaagc ttggaatatg    2160
tctgaatgtg aggtctgtg tcaacctggt gaatattctg cagatggctt tgcaccttgc    2220
cagctctgtg ccctgggcac gttccagcct gaagctggtc gaacttcctg cttcccctgt    2280
ggaggaggcc ttgccaccaa acatcaggga gctacttcct ttcaggactg tgaaaccaga    2340
gttcaatgtt cacctggaca tttctacaac accaccactc accgatgtat tcgttgccca    2400
gtgggaacat accagcctga atttggaaaa ataattgtg tttcttgccc aggaaatact    2460
acgactgact tgatggctc cacaaacata acccagtgta aaaacagaag atgtggaggg    2520
gagctgggag atttcactgg gtacattgaa tccccaaact acccaggcaa ttacccagcc    2580
aacaccgagt gtacgtggac catcaaccca ccccccaagc gccgcatcct gatcgtggtc    2640
cctgagatct tcctgcccat agaggacgac tgtggggact atctggtgat gcggaaaacc    2700
tcttctccaa ttctgtgaca acatatgaaa cctgccagac ctacgaacgc cccatcgcct    2760
tcacctccag gtcaaagaag ctgtggattc agttcaagtc caatgaaggg aacagcgcta    2820
gagggttcca ggtcccatac gtgacatatg atgaggacta ccaggaactc attgaagaca    2880
tagttcgaga tggcaggctc tatgcatctg agaaccatca ggaaatactt aaggataaga    2940
aacttatcaa ggctctgttt gatgtcctgg cccatcccca gaactatttc aagtacacag    3000
cccaggagtc ccgagagatg tttccaagat cgttcatccg attgctacgt tccaaagtgt    3060
ccaggttttt gagaccttac aaatga                                        3086
```

<210> SEQ ID NO 66
<211> LENGTH: 1028
<212> TYPE: PRT
<213> ORGANISM: Homo sapiens

<400> SEQUENCE: 66

```
Met Gly Val Ala Gly Arg Asn Arg Pro Gly Ala Trp Ala Val Leu
1               5                   10                  15

Leu Leu Leu Leu Leu Leu Pro Pro Leu Leu Leu Ala Gly Ala Val
                20                  25                  30

Pro Pro Gly Arg Gly Arg Ala Ala Gly Pro Gln Glu Asp Val Asp Glu
        35                  40                  45

Cys Ala Gln Gly Leu Asp Asp Cys His Ala Asp Ala Leu Cys Gln Asn
    50                  55                  60

Thr Pro Thr Ser Tyr Lys Cys Ser Cys Lys Pro Gly Tyr Gln Gly Glu
65                  70                  75                  80

Gly Arg Gln Cys Glu Asp Ile Asp Glu Cys Gly Asn Glu Leu Asn Gly
                85                  90                  95

Gly Cys Val His Asp Cys Leu Asn Ile Pro Gly Asn Tyr Arg Cys Thr
            100                 105                 110

Cys Phe Asp Gly Phe Met Leu Ala His Asp Gly His Asn Cys Leu Asp
```

-continued

```
            115                 120                 125
Val Asp Glu Cys Leu Glu Asn Asn Gly Gly Cys Gln His Thr Cys Val
            130                 135                 140

Asn Val Met Gly Ser Tyr Glu Cys Cys Lys Glu Gly Phe Phe Leu
145                 150                 155                 160

Ser Asp Asn Gln His Thr Cys Ile His Arg Ser Glu Glu Gly Leu Ser
                165                 170                 175

Cys Met Asn Lys Asp His Gly Cys Ser His Ile Cys Lys Glu Ala Pro
            180                 185                 190

Arg Gly Ser Val Ala Cys Glu Cys Arg Pro Gly Phe Glu Leu Ala Lys
            195                 200                 205

Asn Gln Arg Asp Cys Ile Leu Thr Cys Asn His Gly Asn Gly Gly Cys
            210                 215                 220

Gln His Ser Cys Asp Asp Thr Ala Asp Gly Pro Glu Cys Ser Cys His
225                 230                 235                 240

Pro Gln Tyr Lys Met His Thr Asp Gly Arg Ser Cys Leu Glu Arg Glu
                245                 250                 255

Asp Thr Val Leu Glu Val Thr Glu Ser Asn Thr Thr Ser Val Val Asp
            260                 265                 270

Gly Asp Lys Arg Val Lys Arg Leu Leu Met Glu Thr Cys Ala Val
            275                 280                 285

Asn Asn Gly Gly Cys Asp Arg Thr Cys Lys Asp Thr Ser Thr Gly Val
            290                 295                 300

His Cys Ser Cys Pro Val Gly Phe Thr Leu Gln Leu Asp Gly Lys Thr
305                 310                 315                 320

Cys Lys Asp Ile Asp Glu Cys Gln Thr Arg Asn Gly Gly Cys Asp His
                325                 330                 335

Phe Cys Lys Asn Ile Val Gly Ser Phe Asp Cys Gly Cys Lys Lys Gly
            340                 345                 350

Phe Lys Leu Leu Thr Asp Glu Lys Ser Cys Gln Asp Val Asp Glu Cys
            355                 360                 365

Ser Leu Asp Arg Thr Cys Asp His Ser Cys Ile Asn His Pro Gly Thr
370                 375                 380

Phe Ala Cys Ala Cys Asn Arg Gly Tyr Thr Leu Tyr Gly Phe Thr His
385                 390                 395                 400

Cys Gly Asp Thr Asn Glu Cys Ser Ile Asn Asn Gly Gly Cys Gln Gln
                405                 410                 415

Val Cys Val Asn Thr Val Gly Ser Tyr Glu Cys Gln Cys His Pro Gly
            420                 425                 430

Tyr Lys Leu His Trp Asn Lys Lys Asp Cys Val Glu Val Lys Gly Leu
            435                 440                 445

Leu Pro Thr Ser Val Ser Pro Arg Val Ser Leu His Cys Gly Lys Ser
450                 455                 460

Gly Gly Gly Asp Gly Cys Phe Leu Arg Cys His Ser Gly Ile His Leu
465                 470                 475                 480

Ser Ser Gly Leu Gln Gly Ala Tyr Ser Val Thr Cys Gly Ser Ser Ser
                485                 490                 495

Pro Leu Arg Asn Lys Gln Gln Lys Ser Asn Asp Ser Ala Phe Gly Asp
            500                 505                 510

Val Thr Thr Ile Arg Thr Ser Val Thr Phe Lys Leu Asn Glu Gly Lys
            515                 520                 525

Cys Ser Leu Lys Asn Ala Glu Leu Phe Pro Glu Gly Leu Arg Pro Ala
530                 535                 540
```

```
Leu Pro Glu Lys His Ser Ser Val Lys Glu Ser Phe Arg Tyr Val Asn
545                 550                 555                 560

Leu Thr Cys Ser Ser Gly Lys Gln Val Pro Gly Ala Pro Gly Arg Pro
                565                 570                 575

Ser Thr Pro Lys Glu Met Phe Ile Thr Val Glu Phe Glu Leu Glu Thr
            580                 585                 590

Asn Gln Lys Glu Val Thr Ala Ser Cys Asp Leu Ser Cys Ile Val Lys
        595                 600                 605

Arg Thr Glu Lys Arg Leu Arg Lys Ala Ile Arg Thr Leu Arg Lys Ala
610                 615                 620

Val His Arg Glu Gln Phe His Leu Gln Leu Ser Gly Met Asn Leu Asp
625                 630                 635                 640

Val Ala Lys Lys Pro Pro Arg Thr Ser Glu Arg Gln Ala Glu Ser Cys
                645                 650                 655

Gly Val Gly Gln Gly His Ala Glu Asn Gln Cys Val Ser Cys Arg Ala
            660                 665                 670

Gly Thr Tyr Tyr Asp Gly Ala Arg Glu Arg Cys Ile Leu Cys Pro Asn
        675                 680                 685

Gly Thr Phe Gln Asn Glu Glu Gly Gln Met Thr Cys Glu Pro Cys Pro
690                 695                 700

Arg Pro Gly Asn Ser Gly Ala Leu Lys Thr Pro Glu Ala Trp Asn Met
705                 710                 715                 720

Ser Glu Cys Gly Gly Leu Cys Gln Pro Gly Glu Tyr Ser Ala Asp Gly
                725                 730                 735

Phe Ala Pro Cys Gln Leu Cys Ala Leu Gly Thr Phe Gln Pro Glu Ala
            740                 745                 750

Gly Arg Thr Ser Cys Phe Pro Cys Gly Gly Gly Leu Ala Thr Lys His
        755                 760                 765

Gln Gly Ala Thr Ser Phe Gln Asp Cys Glu Thr Arg Val Gln Cys Ser
770                 775                 780

Pro Gly His Phe Tyr Asn Thr Thr Thr His Arg Cys Ile Arg Cys Pro
785                 790                 795                 800

Val Gly Thr Tyr Gln Pro Glu Phe Gly Lys Asn Asn Cys Val Ser Cys
                805                 810                 815

Pro Gly Asn Thr Thr Thr Asp Phe Asp Gly Ser Thr Asn Ile Thr Gln
            820                 825                 830

Cys Lys Asn Arg Arg Cys Gly Gly Glu Leu Gly Asp Phe Thr Gly Tyr
        835                 840                 845

Ile Glu Ser Pro Asn Tyr Pro Gly Asn Tyr Pro Ala Asn Thr Glu Cys
850                 855                 860

Thr Trp Thr Ile Asn Pro Pro Lys Arg Arg Ile Leu Ile Val Val
865                 870                 875                 880

Pro Glu Ile Phe Leu Pro Ile Glu Asp Asp Cys Gly Asp Tyr Leu Val
                885                 890                 895

Met Arg Lys Thr Ser Ser Ser Asn Ser Val Thr Thr Tyr Glu Thr Cys
            900                 905                 910

Gln Thr Tyr Glu Arg Pro Ile Ala Phe Thr Ser Arg Ser Lys Lys Leu
        915                 920                 925

Trp Ile Gln Phe Lys Ser Asn Glu Gly Asn Ser Ala Arg Gly Phe Gln
930                 935                 940

Val Pro Tyr Val Thr Tyr Asp Glu Asp Tyr Gln Glu Leu Ile Glu Asp
945                 950                 955                 960
```

Ile Val Arg Asp Gly Arg Leu Tyr Ala Ser Glu Asn His Gln Glu Ile
              965                 970                 975

Leu Lys Asp Lys Lys Leu Ile Lys Ala Leu Phe Asp Val Leu Ala His
          980                 985                 990

Pro Gln Asn Tyr Phe Lys Tyr Thr Ala Gln Glu Ser Arg Glu Met Phe
      995                 1000                1005

Pro Arg Ser Phe Ile Arg Leu Leu Arg Ser Lys Val Ser Arg Phe
    1010                1015                1020

Leu Arg Pro Tyr Lys
    1025

<210> SEQ ID NO 67
<211> LENGTH: 27
<212> TYPE: DNA
<213> ORGANISM: Artificial Sequence
<220> FEATURE:
<223> OTHER INFORMATION: VEGF cDNA Forward primer

<400> SEQUENCE: 67
ccgctcgagg cacccatggc agaagga                                      27

<210> SEQ ID NO 68
<211> LENGTH: 32
<212> TYPE: DNA
<213> ORGANISM: Artificial Sequence
<220> FEATURE:
<223> OTHER INFORMATION: VEGF cDNA Reverse primer

<400> SEQUENCE: 68
gctctagatt atcaccgcct cggcttgtca ca                                32

<210> SEQ ID NO 69
<211> LENGTH: 21
<212> TYPE: DNA
<213> ORGANISM: Artificial Sequence
<220> FEATURE:
<223> OTHER INFORMATION: SCUBE1 Forward

<400> SEQUENCE: 69
tgcggcggcg agcttggtga c                                            21

<210> SEQ ID NO 70
<211> LENGTH: 24
<212> TYPE: DNA
<213> ORGANISM: Artificial Sequence
<220> FEATURE:
<223> OTHER INFORMATION: SCUBE1 Reverse

<400> SEQUENCE: 70
tttggagcgc agcagtttga tgaa                                         24

<210> SEQ ID NO 71
<211> LENGTH: 24
<212> TYPE: DNA
<213> ORGANISM: Artificial Sequence
<220> FEATURE:
<223> OTHER INFORMATION: SCUBE2 Forward

<400> SEQUENCE: 71
tcttgcccag gaaatactac gact                                         24

<210> SEQ ID NO 72
<211> LENGTH: 22
<212> TYPE: DNA

```
<213> ORGANISM: Artificial Sequence
<220> FEATURE:
<223> OTHER INFORMATION: SCUBE2 Reverse

<400> SEQUENCE: 72
tgggccagga catcaaacag ag                                      22

<210> SEQ ID NO 73
<211> LENGTH: 24
<212> TYPE: DNA
<213> ORGANISM: Artificial Sequence
<220> FEATURE:
<223> OTHER INFORMATION: SCUBE3 Forward

<400> SEQUENCE: 73
tggcccaatg caagaatcgt cagt                                    24

<210> SEQ ID NO 74
<211> LENGTH: 21
<212> TYPE: DNA
<213> ORGANISM: Artificial Sequence
<220> FEATURE:
<223> OTHER INFORMATION: SCUBE3 Reverse

<400> SEQUENCE: 74
tgggctagca cctcaaagaa g                                       21

<210> SEQ ID NO 75
<211> LENGTH: 20
<212> TYPE: DNA
<213> ORGANISM: Artificial Sequence
<220> FEATURE:
<223> OTHER INFORMATION: GAPDH Forward

<400> SEQUENCE: 75
gccaaaaggg tcatcatctc                                         20

<210> SEQ ID NO 76
<211> LENGTH: 20
<212> TYPE: DNA
<213> ORGANISM: Artificial Sequence
<220> FEATURE:
<223> OTHER INFORMATION: GAPDH Reverse

<400> SEQUENCE: 76
accacctggt gctcagtgta                                         20

<210> SEQ ID NO 77
<211> LENGTH: 23
<212> TYPE: DNA
<213> ORGANISM: Artificial Sequence
<220> FEATURE:
<223> OTHER INFORMATION: mouse Scube1 Forward

<400> SEQUENCE: 77
cggcggcgaa cttggtgact aca                                     23

<210> SEQ ID NO 78
<211> LENGTH: 23
<212> TYPE: DNA
<213> ORGANISM: Artificial Sequence
<220> FEATURE:
<223> OTHER INFORMATION: mouse Scube1 Reverse

<400> SEQUENCE: 78
ttgataaagg accgggggaa cat                                     23
```

<210> SEQ ID NO 79
<211> LENGTH: 24
<212> TYPE: DNA
<213> ORGANISM: Artificial Sequence
<220> FEATURE:
<223> OTHER INFORMATION: mouse Scube2 Forward

<400> SEQUENCE: 79
tgactacctg gtgatgcgga aaac                                          24

<210> SEQ ID NO 80
<211> LENGTH: 22
<212> TYPE: DNA
<213> ORGANISM: Artificial Sequence
<220> FEATURE:
<223> OTHER INFORMATION: mouse Scube2 Reverse

<400> SEQUENCE: 80
cagtggcgtg tgggaagagt ca                                            22

<210> SEQ ID NO 81
<211> LENGTH: 21
<212> TYPE: DNA
<213> ORGANISM: Artificial Sequence
<220> FEATURE:
<223> OTHER INFORMATION: mouse Scube3 Forward

<400> SEQUENCE: 81
tgctccccgg gccactacta t                                             21

<210> SEQ ID NO 82
<211> LENGTH: 24
<212> TYPE: DNA
<213> ORGANISM: Artificial Sequence
<220> FEATURE:
<223> OTHER INFORMATION: mouse Scube3 Reverse

<400> SEQUENCE: 82
agcgctgttg gcctcactgg tctt                                          24

<210> SEQ ID NO 83
<211> LENGTH: 21
<212> TYPE: DNA
<213> ORGANISM: Artificial Sequence
<220> FEATURE:
<223> OTHER INFORMATION: SCUBE2 Forward

<400> SEQUENCE: 83
gcacacgcac gcgcgcacac a                                             21

<210> SEQ ID NO 84
<211> LENGTH: 21
<212> TYPE: DNA
<213> ORGANISM: Artificial Sequence
<220> FEATURE:
<223> OTHER INFORMATION: SCUBE2 Reverse

<400> SEQUENCE: 84
gaagggtgca gagggtgtgc t                                             21

<210> SEQ ID NO 85
<211> LENGTH: 25
<212> TYPE: DNA
<213> ORGANISM: Artificial Sequence
<220> FEATURE:

<223> OTHER INFORMATION: mouse Gapdh Forward

<400> SEQUENCE: 85
atcatccctg catccactgg tgctg                                                    25

<210> SEQ ID NO 86
<211> LENGTH: 25
<212> TYPE: DNA
<213> ORGANISM: Artificial Sequence
<220> FEATURE:
<223> OTHER INFORMATION: mouse Gapdh Reverse

<400> SEQUENCE: 86
tgatggcatt caagagagta gggag                                                    25

<210> SEQ ID NO 87
<211> LENGTH: 20
<212> TYPE: DNA
<213> ORGANISM: Artificial Sequence
<220> FEATURE:
<223> OTHER INFORMATION: SCUBE1 Forward

<400> SEQUENCE: 87
aacatcccgg ggaactacag                                                          20

<210> SEQ ID NO 88
<211> LENGTH: 20
<212> TYPE: DNA
<213> ORGANISM: Artificial Sequence
<220> FEATURE:
<223> OTHER INFORMATION: SCUBE1 Reverse

<400> SEQUENCE: 88
gcagccacca ttattgtcct                                                          20

<210> SEQ ID NO 89
<211> LENGTH: 20
<212> TYPE: DNA
<213> ORGANISM: Artificial Sequence
<220> FEATURE:
<223> OTHER INFORMATION: SCUBE2 Forward

<400> SEQUENCE: 89
caggcagagt cctgtggagt                                                          20

<210> SEQ ID NO 90
<211> LENGTH: 20
<212> TYPE: DNA
<213> ORGANISM: Artificial Sequence
<220> FEATURE:
<223> OTHER INFORMATION: SCUBE2 Reverse

<400> SEQUENCE: 90
taaaatgcag cgttctcgtg                                                          20

<210> SEQ ID NO 91
<211> LENGTH: 18
<212> TYPE: DNA
<213> ORGANISM: Artificial Sequence
<220> FEATURE:
<223> OTHER INFORMATION: SCUBE3 Forward

<400> SEQUENCE: 91
cctgcttgtc ctgctggt                                                            18

```
<210> SEQ ID NO 92
<211> LENGTH: 20
<212> TYPE: DNA
<213> ORGANISM: Artificial Sequence
<220> FEATURE:
<223> OTHER INFORMATION: SCUBE3 Reverse

<400> SEQUENCE: 92
tcgatgtggc agttgtcagt                                              20

<210> SEQ ID NO 93
<211> LENGTH: 19
<212> TYPE: DNA
<213> ORGANISM: Artificial Sequence
<220> FEATURE:
<223> OTHER INFORMATION: GAPDH Forward

<400> SEQUENCE: 93
tgaaggtcgg agtcaacgg                                               19

<210> SEQ ID NO 94
<211> LENGTH: 22
<212> TYPE: DNA
<213> ORGANISM: Artificial Sequence
<220> FEATURE:
<223> OTHER INFORMATION: GAPDH Reverse

<400> SEQUENCE: 94
agagttaaaa gcagccctgg tg                                           22

<210> SEQ ID NO 95
<211> LENGTH: 29
<212> TYPE: DNA
<213> ORGANISM: Artificial Sequence
<220> FEATURE:
<223> OTHER INFORMATION: Scube2-5'Flox F1

<400> SEQUENCE: 95
atagtcgact gttgtccagt atctgttgc                                    29

<210> SEQ ID NO 96
<211> LENGTH: 31
<212> TYPE: DNA
<213> ORGANISM: Artificial Sequence
<220> FEATURE:
<223> OTHER INFORMATION: Scube2-5'Flox R1

<400> SEQUENCE: 96
atagcggccg ctacgacacc ctgggataaa g                                 31

<210> SEQ ID NO 97
<211> LENGTH: 23
<212> TYPE: DNA
<213> ORGANISM: Artificial Sequence
<220> FEATURE:
<223> OTHER INFORMATION: Scube2-3'Flox F2

<400> SEQUENCE: 97
ggccatgtcc ctgaagaaaa cta                                          23

<210> SEQ ID NO 98
<211> LENGTH: 22
<212> TYPE: DNA
<213> ORGANISM: Artificial Sequence
<220> FEATURE:
<223> OTHER INFORMATION: Scube2-3'Flox R2
```

```
<400> SEQUENCE: 98
ttatggggcc aagacactca aa                                            22

<210> SEQ ID NO 99
<211> LENGTH: 22
<212> TYPE: DNA
<213> ORGANISM: Artificial Sequence
<220> FEATURE:
<223> OTHER INFORMATION: Scube2-Null F3

<400> SEQUENCE: 99
ctggggcctc tgggacacta tt                                            22

<210> SEQ ID NO 100
<211> LENGTH: 23
<212> TYPE: DNA
<213> ORGANISM: Artificial Sequence
<220> FEATURE:
<223> OTHER INFORMATION: Scube2-Null R3

<400> SEQUENCE: 100
gttatggggc caagacactc aaa                                           23

<210> SEQ ID NO 101
<211> LENGTH: 25
<212> TYPE: DNA
<213> ORGANISM: Artificial Sequence
<220> FEATURE:
<223> OTHER INFORMATION: Cre Forward

<400> SEQUENCE: 101
ttaccggtcg atgcaacgag tgatg                                         25

<210> SEQ ID NO 102
<211> LENGTH: 23
<212> TYPE: DNA
<213> ORGANISM: Artificial Sequence
<220> FEATURE:
<223> OTHER INFORMATION: Cre Reverse

<400> SEQUENCE: 102
gtgaaacagc attgctgtca ctt                                           23
```

INHIBITION OF SCUBE2, A NOVEL VEGFR2 CO-RECEPTOR, SUPPRESSES TUMOR ANGIOGENESIS

REFERENCE TO RELATED APPLICATION

This application is a division of and claims priority to U.S. application Ser. No. 16/091,164 filed Oct. 4, 2018, which the status is issued as U.S. Pat. No. 11,066,466. The application Ser. No. 16/091,164 is a national stage application (under 35 U.S.C., 371) of PCT/US2017/026855 filed on 10 Apr. 2017, which claims priority to U.S. provisional application 62/322,626 filed on 14 Apr. 2016, all of which are herein incorporated by reference in their entireties.

FIELD OF THE INVENTION

The present invention relates generally to anti-angiogenic therapy, more specifically to anti-SCUBE2 antibodies for anti-angiogenic therapy.

BACKGROUND OF THE INVENTION

Vascular endothelial growth factor (VEGF) is a major mediator of angiogenesis; it binds to its receptor VEGFR2 (a receptor tyrosine kinase, RTK) on the surface of endothelial cells (ECs) and triggers dimerization and trans-phosphorylation to activate signaling cascades including p44/42 mitogen-activated protein kinases (MAPKs) and AKT required for EC migration, proliferation, and tubulogenesis. These VEGF responses can be further promoted by a small number of VEGFR2 co-receptors such as neuropilins, heparan sulfate proteoglycans, CD44, and CD146. However, additional co-receptors for VEGFR2 that regulate VEGF-induced angiogenesis might exist and remain to be discovered.

SCUBE2 is the second member of a small, evolutionarily conserved gene family composed of three different genes (SCUBE1, 2, and 3) originally identified from human ECs. The genes encode ~1,000-amino acid polypeptides organized in a modular fashion with five protein domains: an $NH_2$-terminal signal peptide, nine tandem repeats of EGF-like motifs, a spacer region, three cysteine-rich (CR) repeats, and one CUB domain at the COOH terminus. These SCUBEs can tether on the cell surface as peripheral membrane proteins by two distinct membrane-anchoring mechanisms (i.e., electrostatic and lectin-glycan interactions) via its spacer region and the CR repeats, and function as co-receptors for a number of growth factors. Besides being expressed in the normal endothelium, SCUBE2 is also highly expressed in hypoxic tumor microvasculature. However, whether SCUBE2 can act as a co-receptor for VEGFR2 and its role in VEGF-induced angiogenesis remain to be determined.

SUMMARY OF THE INVENTION

In one aspect, the invention relates to an isolated anti-SCUBE2 antibody or a binding fragment thereof, which comprises an antigen binding region that specifically binds to a target domain located within SCUBE2 (SEQ ID NO: 66) and exhibits a property of inhibiting VEGF-induced angiogenesis, wherein the target domain is selected from the group consisting of the EGF-like motifs 4 to 6 ranging from a.a. position 175 to 323, or the spacer region ranging from a.a. position 441 to 659, or the first cys-rich motif ranging from a.a. position 668 to 725 of SCUBE2 (SEQ ID NO: 66).

In one embodiment, the isolated anti-SCUBE2 antibody or binding fragment thereof of the invention exhibits a property of inhibition of tumor angiogenesis and VEGF-stimulated endothelial cell proliferation and capillary tube formation.

In another embodiment, the isolated anti-SCUBE2 antibody or binding fragment thereof of the invention comprises a heavy chain variable domain $(V_H)$ and a light chain variable domain $(V_L)$, wherein:
(a) the $V_H$ comprises the amino acid sequence of SEQ ID NO: 17, and the $V_L$ comprises the amino acid sequence of SEQ ID NO: 18; or
(b) the $V_H$ comprises the amino acid sequence of SEQ ID NO: 1, and the $V_L$ comprises the amino acid sequence of SEQ ID NO: 2; or
(c) the $V_H$ comprises the amino acid sequence of SEQ ID NO: 33, and the $V_L$ comprises the amino acid sequence of SEQ ID NO: 34; or
(d) the $V_H$ comprises the amino acid sequence of SEQ ID NO: 49, and the $V_L$ comprises the amino acid sequence of SEQ ID NO: 50.

In another embodiment, the $V_H$ and $V_L$ of the anti-SCUBE2 antibody each comprise complementarity determining region (CDR) 1, CDR2, CDR3 as follows:
(i) the $V_H$ comprises a CDR1 comprising the amino acid sequence of SEQ ID NO: 19, a CDR2 comprising the amino acid sequence of SEQ ID NO: 20, and a CDR3 comprising the amino acid sequence of SEQ ID NO: 21; and the $V_L$ comprises a CDR1 comprising the amino acid sequence of SEQ ID NO: 22, a CDR2 comprising the amino acid sequence of SEQ ID NO: 23, and a CDR3 comprising the amino acid sequence of SEQ ID NO: 24; or
(ii) the $V_H$ comprises a CDR1 comprising the amino acid sequence of SEQ ID NO: 3, a CDR2 comprising the amino acid sequence of SEQ ID NO: 4, and a CDR3 comprising the amino acid sequence of SEQ ID NO: 5; and the $V_L$ comprises a CDR1 comprising the amino acid sequence of SEQ ID NO: 6, a CDR2 comprising the amino acid sequence of SEQ ID NO: 7, and a CDR3 comprising the amino acid sequence of SEQ ID NO: 8; or
(iii) the $V_H$ comprises a CDR1 comprising the amino acid sequence of SEQ ID NO: 35, a CDR2 comprising the amino acid sequence of SEQ ID NO: 36, and a CDR3 comprising the amino acid sequence of SEQ ID NO: 37; and the $V_L$ comprises a CDR1 comprising the amino acid sequence of SEQ ID NO: 38, a CDR2 comprising the amino acid sequence of SEQ ID NO: 39, and a CDR3 comprising the amino acid sequence of SEQ ID NO: 40; or
(iv) the $V_H$ comprises a CDR1 comprising the amino acid sequence of SEQ ID NO: 51, a CDR2 comprising the amino acid sequence of SEQ ID NO: 52, and a CDR3 comprising the amino acid sequence of SEQ ID NO: 53; and the $V_L$ comprises a CDR1 comprising the amino acid sequence of SEQ ID NO: 54, a CDR2 comprising the amino acid sequence of SEQ ID NO: 55, and a CDR3 comprising the amino acid sequence of SEQ ID NO: 56.

In another embodiment, the isolated anti-SCUBE2 antibody or binding fragment thereof of the invention is a monoclonal antibody, is humanized, is a fusion protein, or is selected from the group consisting of a Fv fragment, a fragment antigen-binding (Fab) fragment, a F(ab'), fragment, a Fab' fragment, a Fd' fragment, and a Fd fragment, and a single chain antibody variable fragment (scFv).

In another embodiment, the isolated anti-SCUBE2 antibody or binding fragment of the invention is encapsulated within a liposome.

In another aspect, the invention relates to a pharmaceutical composition comprising: (i) a therapeutically effective amount of an isolated anti-SCUBE2 antibody or a binding fragment thereof of the invention; and (ii) a therapeutically effective amount of an anti-VEGF antibody specifically against VEGF.

In one embodiment, the $V_1$ and the $V_L$ of the anti-SCUBE2 antibody in the pharmaceutical composition comprises amino acid sequence as follows: (i) the $V_H$ comprises the amino acid sequence of SEQ ID NO: 17, and the $V_L$ comprises the amino acid sequence of SEQ ID NO: 18, or (ii) the $V_H$ comprises a CDR1 comprising the amino acid sequence of SEQ ID NO: 19, a CDR2 comprising the amino acid sequence of SEQ ID NO: 20, and a CDR3 comprising the amino acid sequence of SEQ ID NO: 21; and the $V_L$ comprises a CDR1 comprising the amino acid sequence of SEQ ID NO: 22, a CDR2 comprising the amino acid sequence of SEQ ID NO: 23, and a CDR3 comprising the amino acid sequence of SEQ ID NO: 24.

In another embodiment, the anti-SCUBE2 antibody in the pharmaceutical composition may be a monoclonal antibody, a chimeric antibody, or a humanized antibody.

In another embodiment, the isolated of the anti-SCUBE2 antibody or binding fragment thereof of the invention exhibits a specific binding affinity for crossreactive epitopes shared by SCUBE2 expressed on human vascular endothelial cells and SCUBE2 expressed on murine vascular endothelial cells.

In another aspect, the invention relates to use of an isolated anti-SCUBE2 antibody or a binding fragment thereof in the manufacture of a medicament for treating a disease that is associated with VEGF-induced angiogenesis in a subject in need thereof. In one embodiment, the disease that is associated with VEGF-induced angiogenesis is at least one selected from the group consisting of tumor, neovascuar eye disorder, persistent hyperplastic vitreous syndrome, diabetic retinopathy, retinopathy of prematurity, choroidal neovascularization, endometriosis, uterine bleeding, ovarian cysts, and ovarian hyperstimulation. In another embodiment, the use of the invention is in combination with use of an anti-VEGF antibody specifically against VEGF in the manufacture of a medicament for treating a disease that is associated with VEGF-induced angiogenesis in a subject in need thereof.

Further in another aspect, the invention relates to use of an isolated anti-SCUBE2 antibody or a binding fragment thereof in the manufacture of a medicament for treating a tumor or for inhibiting tumor angiogenesis and cancer cell growth in a subject in need thereof. Alternatively, the invention relates to an isolated anti-SCUBE2 antibody or a binding fragment thereof for use in treating a disease that is associated with VEGF-induced angiogenesis, or in treating a tumor or inhibiting tumor angiogenesis and cancer cell growth in a subject in need thereof. The anti-SCUBE2 antibody or binding fragment thereof of the invention may be used in combination with an anti-VEGF antibody such as bevacizumab for use in treating a disease that is associated with VEGF-induced angiogenesis, or for use in treating a tumor, or inhibiting tumor angiogenesis and cancer cell growth in a subject in need thereof.

The invention is also relates to a method for treating a disease that is associated with VEGF-induced angiogenesis, or for treating a tumor or inhibiting tumor angiogenesis and cancer cell growth in a subject in need thereof. The method comprises administering a therapeutically effective amount of the anti-SCUBE2 antibody or binding fragment thereof of the invention to the subject in need thereof. The method may further comprises administering a therapeutically effective amount of an anti-VEGF antibody to the subject in need thereof.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
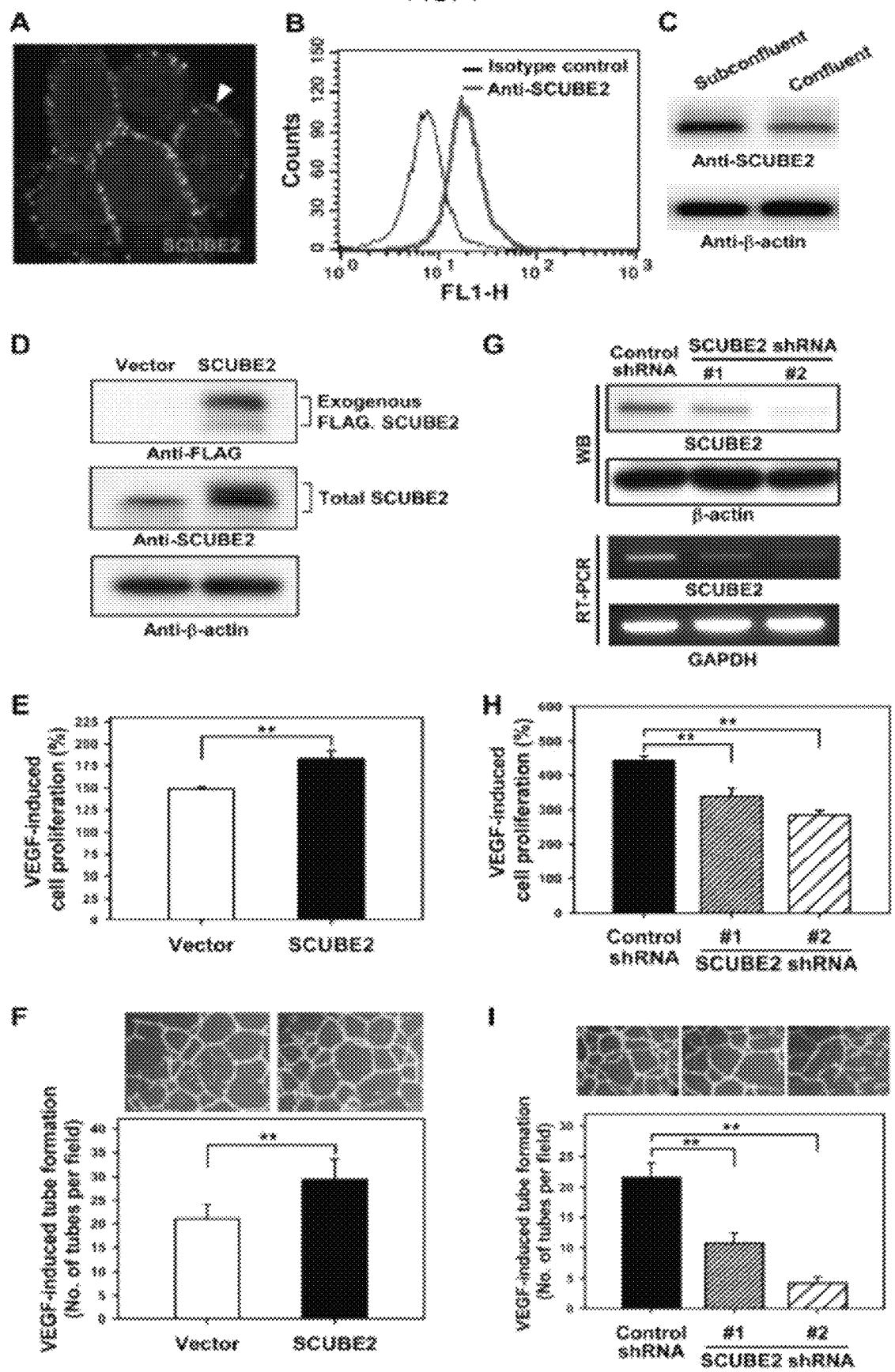
FIG. 1 shows that SCUBE2 is expressed at the cell surface of human umbilical vein endothelial cells (HUVECs) and modulates vascular endothelial growth factor (VEGF)-induced HUVEC proliferation and tube formation. A and B, SCUBE2 immunofluorescence staining (in green) and flow cytometry. Arrowhead indicates SCUBE2 expressed on EC membrane. Nuclei are stained with DAPI in blue. C, Western blot analysis of SCUBE2 protein expression in subconfluent (proliferating) and confluent (non-proliferating) HUVECs. D-F, SCUBE2 overexpression enhances VEGF-induced HUVEC proliferation and tubulogenesis. Exogenous SCUBE2 expressed in HUVECs transduced with an empty lentivirus or recombinant lentivirus encoding an FLAG-tagged SCUBE2 (D). Effect of SCUBE2 overexpression on VEGF-induced HUVEC cell growth (E). Data are mean±SD and represent percent increased relative to non-stimulated cells from 3 independent experiments. , P<: 0.01. In vitro MATRIGEL™ angiogenesis assay of effect of SCUBE2 overexpression on VEGF-induced tube formation (F). Representative images are shown at top and quantified by counting the total number of tubules per field. Data are means±SD calculated from 3 independent experiments, , P<0.01. G-I, SCUBE2 knockdown decreases VEGF-induced HUVEC proliferation and tube formation. SCUBE2 expression was downregulated by two independent SCUBE2-targeting shRNA lentiviruses (SCUBE1-shRNA #1 and #2) in HUVECs (G). A luciferase shRNA lentivirus was a negative control (Control shRNA). Effect of SCUBE2 knockdown on VEGF-induced (H) HUVEC cell growth and (1) tube formation. Data are mean±SD and represent percent increased relative to non-stimulated cells from 3 independent experiments. , P<0.01. In vitro MATRIGEL™ angiogenesis assay of effect of SCUBE2 knockdowns on VEGF-induced tube formation. Representative images are shown at top and quantified by counting the total number of tubules per field (I). Data are mean±SD calculated from 3 independent experiments, , P<0.01.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

Unless otherwise defined, all technical and scientific terms used herein have the same meaning as commonly understood by one of ordinary skill in the art to which this invention pertains. In the case of conflict, the present document, including definitions will control.

The term "antibody fragment" or "fragment thereof" is used herein, for purposes of the specification and claims, to mean a portion or fragment of an intact antibody molecule, wherein the fragment retains antigen-binding function; i.e., F(ab')2. Fab', Fab, Fv, single chain Fv ("scFv"), Fd' and Fd fragments. Methods for producing the various fragments from mAbs are well known to those skilled in the art.

The terms "specific binding affinity or binding specificity for crossreactive epitopes shared by SCUBE2 expressed on human vascular endothelial cells and SCUBE2 expressed on murine vascular endothelial cells" (or "binding specificity for crossreactive epitopes between human SCUBE2 and murine SCUBE2") are used herein to mean the property of an anti-SCUBE2 antibody to bind a cross-reactive epitope present on both human SCUBE2 and murine SCUBE2, wherein (a) such epitope is accessible on the surface of the vascular endothelial cells expressing the SCUBE2; (b) the binding to the SCUBE2 epitope present on murine endothelial cells is greater than the binding exhibited by an isotype control immunoglobulin, and "greater than" can be measured quantitatively as the binding of the anti-SCUBE2 mAb minus one standard deviation needs to be larger than the binding of the isotype control immunoglobulin plus 1 standard deviation, as will be more apparent in the following examples: and (c) the binding of the anti-SCUBE2 antibody to the SCUBE2 expressed on murine endothelial cells is at least two fold less when compared to the binding of the anti-SCUBE2 antibody to the SCUBE2 expressed on human endothelial cells, as detected in a standard assay for immunoreactivity.

A co-receptor is a cell surface receptor that binds a signalling molecule in addition to a primary receptor in order to facilitate ligand recognition and initiate biological processes. The nucleotide sequence of human SCUBE2 cDNA (SEQ ID NO: 65); the amino acid sequence of human SCUBE2 (SEQ ID NO: 66).

Abbreviation: ECs, endothelial cells; EC-KO mice, EC-specific Scube2-knockout mice; LLC, Lewis lung carcinoma; AP, alkaline phosphatase; HIF, hypoxia-inducible factor; HUVEC, human umbilical vein endothelial cell; KO, knockout; MAPK, mitogen-activated protein kinase; MLEC, mouse lung endothelial cell; RTK, receptor tyrosine kinase; SCUBE2, Signal peptide-complement protein C1r/C1s, Uegf, and Bmp1 (CUB)-epidermal growth factor (EGF) domain-containing protein 2; shRNA, short hairpin RNA; VEGF, vascular endothelial growth factor; VEGFR2, vascular endothelial growth factor receptor 2.

Utility/Indications
(1) pathological tumor angiogenesis; and
(2) neovascular eye diseases SCUBE2 is a peripheral membrane protein expressed in normal and tumor vascular endothelial cells (ECs); however, its role in angiogenesis remains poorly understood. We discovered SCUBE2 as a co-receptor for VEGFR2 and its role in VEGF-induced angiogenesis. SCUBE2 was upregulated by hypoxia-inducible factor (HIF-1α) in response to hypoxic conditions and interacted with VEGFR2 in human ECs, where it acted as a co-receptor with VEGFR2 to facilitate VEGF binding and enhance its downstream signaling, thus promoting VEGF-induced angiogenesis and tumor angiogenesis. This SCUBE2 and VEGFR2 interaction and its enhanced signal transduction could be inhibited by endothelial Scube2 gene inactivation, SCUBE2 shRNA-mediated knockdown, as well as anti-SCUBE2 mAb neutralization both in vitro and in vivo. Endothelial Scube2 knockout (EC-KO mice) showed no defects in vascular development but did show impaired VEGF-induced neovascularization in implanted MATRIGEL™ plugs and impaired recovery of blood flow after induced hind-limb ischemia. SCUBE2 is a novel co-receptor for VEGFR2 that regulates the VEGF-induced tube formation and proliferation of ECs by fine-tuning VEGFR2-mediated signaling, especially during postnatal angiogenesis induced by ischemia or under hypoxic conditions. Targeting this SCUBE2 function in tumor ECs may represent a potential anti-tumor modality via inhibiting tumor angiogenesis.

We discovered that SCUBE2 acts as a co-receptor for VEGFR2 to potentiate VEGF binding to VEGFR2 and augment its signals, including VEGFR2 phosphorylation and p44/42 mitogen-activated protein kinase (MAPK)/Akt activation, thus promoting cell proliferation and tubule formation in ECs. Physiological angiogenesis remained normal with endothelial ablation of Scube2 in mice, pathological angiogenesis in experimental tumors was altered, for smaller tumors and reduced microvascular density. To simulate the angiogenic environment of the tumor, Scube2-deficient ECs were isolated and propagated in vitro with VEGF. Mutant ECs showed markedly reduced binding of VEGF, proliferation and sprouting responses to VEGF as well as downstream signal activation. Furthermore, anti-SCUBE2 and anti-VEGF monoclonal antibodies had an additive inhibitory effect on xenografted lung tumors. Together, our findings establish SCUBE2 is a key regulator of VEGF responses in tumor ECs and suggest that an anti-SCUBE2 strategy has great potential in combination anti-angiogenic cancer therapy.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Antibodies and reagents. Anti-SCUBE2, anti-HIF-1α, and anti-phospho-tyrosine polyclonal antibodies were from GeneTex (Irvine, Calif.). Anti-phospho-VEGFR2 (Thr1059), anti-phospho-MAPK p44/p42 (Thr202/Tyr204), anti-MAPK p44/p42, anti-phospho-AKT (Ser473), anti-AKT, and anti-EGFR antibodies were from Cell Signaling Technology (Danvers. Mass.). Anti-VEGFR2 and anti-VEGF antibodies were from Thermo Scientific (Rockford, Ill.) and Santa Cruz Biotechnology (Santa Cruz, Calif.), respectively. Anti-CD31, anti-phospho-serine % threonine, anti-VEGFR1, and anti-neuropilin-1 antibodies were from Abcam (Cambridge, Mass.). Anti-Ki67 and anti-β-actin antibodies were from DAKO Cytomatation (Glostrup, Denmark) and NOVUS Biologicals (Littleton, Colo.), respectively. Recombinant $VEGF_{165}$ protein was from R&D Systems (Minneapolis, Minn.).

Generation of anti-SCUBE2 monoclonal antibodies. Antibody specific against SCUBE2 was generated as follows. Splenocytes from BALB/c mice immunized with purified recombinant SCUBE2-spacer region (amino acids 445 to 667) produced from HEK-293T cells were fused with myeloma cells (SP2/O) to produce hydridomas. The hybridoma cell lines were prepared and subcloned as described previously (Hadas et al. "Production of monoclonal antibodies. The effect of hybridoma concentration on the yield of antibody-producing clones" J Immunol Methods 1987; 96:3-6). The hybridoma cell lines positive for SCUBE2 not SCUBE1 and 3 were identified as described (Tu et al "Localization and characterization of a novel protein SCUBE1 in human platelets" Cardiovasc Res. 2006; 71:486-95; Cheng et al "SCUBE2 suppresses breast tumor cell proliferation and confers a favorable prognosis in invasive breast cancer" Cancer Res. 2009; 69:3634-41).

Generation of conditional $Scube2^{Flox/Flax}$ and endothelium-specific Scube2-knockout (EC-KO) mice. The conditional $Scube2^{Flox}$ allele containing two loxP sites separated by 65 kb of genomic sequence covering exons 2 to 21 was produced as described. To generate endothelial-specific conditional KO mice, transgenic mice expressing Cre recombinase under the control of the Tie2 promoter and heterozygous for Scube2 (Tie2-Cre; $Scube2^{+/-}$) were crossed with $Scube2^{Flox/Flax}$ animals to obtain experimental Tie2-Cre: $Scube2^{Flax/+}$ (control) and Tie2-Cre: $Scube2^{Flox/-}$ (EC-KO) mice. Male mice were mainly used for all phenotyping comparisons in each genotype group (n=5 or more as specified). All animal experiments were approved by the Institute Animal Care and Utilization Committee, Academia Sinica.

Tumor xenografts. Xenograft tumors were generated by injecting $1 \times 10^6$ melanoma cells (B16F10) or Lewis lung carcinoma cells (LLC) subcutaneously on flanks of control and EC-KO mice. Tumor size was measured twice a week by using digital calipers and calculated by length×width×height×0.5236 (in mm$^3$). After tumor growth for 16 d, the tumors were fixed and embedded in paraffin for tissue sectioning. Pimonidazole and APO-BRDU™ (TUNEL) apoptosis reagents were used according to manufacturer's instructions. Tissue blood vessels and proliferation from LLC and B16F10 tumors were visualized by using CD31 and Ki-67 antibodies, respectively.

MATRIGEL™ angiogenesis assay. The angiogenesis model was based on the use of MATRIGEL™ implants in control or EC-KO mice. An amount of 0.5 ml growth factor-reduced MATRIGEL™ with or without 100 ng/ml VEGF was injected in the mouse flank. The injection was made rapidly with 26G needle to ensure that the contents of the syringe were delivered as a single plug. One week later, plugs were harvested and homogenized in RIPA lysis buffer. After the removal of debris by centrifugation, the hemoglobin concentration was measured by using Drabkin's regent (Sigma-Aldrich). Alternatively, plugs were fixed overnight in 4% paraformaldehyde, embedded in paraffin, sectioned, and stained with anti-CD31 antibody.

Hind-limb ischemia model. The hind-limb ischemia model was performed as previously described.[3] Briefly, the femoral artery of control and EC-KO mice (8 weeks) was exposed, isolated from the femoral nerve and vein, and ligated at two positions 5 mm apart, one just proximal to the groin ligament, and the second distal to it and proximal to the popliteal artery. The skin was closed by interrupted 4-0 sutures. Laser-Doppler flow imaging involved use of the Moor Infrared Laser Doppler Imager with mice under anesthesia at different times before and after surgery. Calf muscles were harvested with mice under anesthesia at 3 weeks after proximal femoral artery ligation and used for CD31 staining.

Aortic ring sprouting assay. Mouse aortic ring sprouting assay was essentially prepared as reported. Aortas were harvested from mice. Remove all extraneous fat, tissue and branching vessels with forceps and a scalpel. Transfer aortas to a petri dish containing OPTI-MEM culture medium, and the aortas were sliced into approximately 0.5 mm-thick ring. The rings were embedded in 1 mg/ml type I collagen and then incubate it at 37° C./5% $CO_2$ for 1 h. OPTI-MEM culture medium supplemented with 2.5% FBS and 30 ng/ml VEGF was added and surround the aortic ring. The number and length of microvessel sprouts were calculated on day 5.

Immunohistochemistry. Tissue sections (5 µm thick) were dewaxed with xylene, rehydrated in graded concentrations of alcohol, treated with 3% $H_2O_2$ for 20 min, washed with PBS, blocked with blocking solution (PBST supplemented with 2% BSA and 2% normal goat serum) for 1 h, and incubated at room temperature overnight with primary antibody. Antibody binding was detected by using horseradish peroxidase-conjugated antibody and stable 3,3'-diaminobenzidine (DAB) peroxidase substrate. Hematoxylin was used for counterstaining.

Primary mouse lung ECs (MLECs) isolation, characterization, and culture. Primary MLECs were generated from lung tissue of control and EC-KO mice as described.[6] Each mouse (6 weeks old) initially received a 100-µl intramuscular injection of heparin (140 U/ml), then 10 min later, mice were anesthetized, and the thoracic cavity was exposed. Cold M199 medium was injected via the right ventricle to flush blood cells from the lung. An amount of 1 ml collagenase A (1 mg/ml) was then quickly instilled through the trachea into the lungs. The lungs were removed and incubated with 5 ml collagenase A for 30 min in 37° C. The cell suspension was filtered through a 70-µm strainer, then centrifuged for 5 min at 1000 rpm. The cell pellet was resuspended in growth medium (M199 medium supplemented with 20% fetal bovine serum, 50 µg/ml EC growth factor, 100 µg/ml heparin, 2 mM glutamine. 100 units/ml penicillin, and 100 µg/ml streptomycin) and plated into a gelatin-coated tissue culture dish for an additional 2 days. Cells were removed by use of trypsin and pooled into one suspension for anti-CD31-PE antibody staining and FACS sorting.

Hypoxia treatment and lentiviral SCUBE2 overexpression/knockdown in HUVECs. HUVECs were purchased from the Bioresource Collection and Research Center (Taiwan) and cultured according to the supplier's recommendations. For hypoxic treatment, HUVECs were exposed to hypoxia (1% $O_2$) by incubation in a $CO_2$ incubator gassed with a mixture of 95% $N_2$/5% $CO_2$. HUVECs were engineered with the full-length SCUBE2 expression vector or empty vector by a self-inactivating leniviral transduction system. We used the vector-based short hairpin RNAs (shRNAs) generated by The RNAi Consortium to knock down the endogenous SCUBE2 in the HUVECs.

Chromatin immunoprecipitation (ChIP). ChIP analysis was as described with the EZ-MAGNA CHIP™ G Kit. Briefly, HUVECs (1×10$^7$ cells) were cross-linked by use of 1% formaldehyde, lysed in 500 µl lysis buffer and sonicated to approximately 500-bp fragments. ChIP involved antibodies against HIF-1α or IgG. The input control DNA or immunoprecipitated DNA was amplified in a 50-µl reaction volume consisting of 2 µl eluted DNA template with primers (Table 1). PCR involved use of Taq polymerase for 35 cycles of 94° C. for 30 sec, 63.5° C. for 30 sec, 72° C. for 40 sec. then 5 min at 72° C. A 10-µl aliquot from each PCR reaction was separated on 1.5% agarose gel.

Luciferase reporter assay. HUVECs were transiently transfected with 4.5 µg SCUBE2 promoter luciferase reporter plasmid (WT, M1, M2, and M3) and internal control (0.45 µg pRL-TK Renilla luciferase plasmid) by using NUCLEOFECTOR™ according to the manufacturer's instructions. Cells were cultured for an additional 2 days, harvested and prepared for reporter assay with the Dual-Luciferase reporter assay system.

EC proliferation assay. The effect of SCUBE2 on EC proliferation was determined by 3-(4,5-dimethylthiazol-2-yl)-2,5-diphenyitetrazolium bromide (MTT) assay as described. Briefly, ECs were trypsinized and plated onto 96-well cell culture plates at 2000 cells/well in 100 µl complete media. The next day, the cells were stimulated with VEGF (100 ng/ml) or control media for 4 days and cell number was examined.

EC tubulogenesis assay. ECs (3×10$^3$ cells pre well) were seeded on MATRIGEL™ in 15-well p-Slide angiogenesis plates with VEGF (100 ng/ml). After 16 hours, the tubulogenesis was determined by counting vessels in 3 random fields per well.

VEGF-alkalne phosphatase (AP) binding assay. The production of AP-tagged VEGF protein and binding experiments were performed essentially as described. The AP-VEGF chimeric ligand was constructed by amplifying the portion of VEGF cDNA using PCR with the following primers: CCG CTC GAG GCA CCC ATG GCA GAA GGA (SEQ ID NO: 67) and GCT CTA GAT TAT CAC CGC CTC GGC TTG TCA CA (SEQ ID NO: 68). The 498 bp amplified fragment was then cloned into the XhoI and XbaI restriction site of APtag-5. The AP-VEGF fusion protein and the control AP proteins were produced by transient transfection into HEK-293T cells. Supernatants of transfected HEK-293T cells were collected, concentrated, and stored. HEK-293T cells overexpressing VEGFR2 alone or together with SCUBE2 and ECs were incubated 4 h in supernatants and washed three times at 4° C. with PBS. Then cells were lysed for 5 min on ice in lysis buffer (25 mM Hepes, pH7.6, 150 mM NaCl, 5 mM EDTA, 10 µg/ml aprotinin, 5 µg/ml leupeptin, 10% glycerol, and 1% Triton X-100). Cell lysates were clarified by centrifugation at 10,000×g for 20 min at 4° C. The AP activity was detected using the p-Nitrophenyl phosphate substrates.

Pull-down assay. Myc-tagged VE-cadherin-FL, D1, and D2 protein (Myc.VE-cadherin-FL, -D1, -D2) was produced using the In vitro transcription/translation method. Recombinant GST-tagged SCUBE2-CUB protein (GST.SCUBF2-CUB) was purified from the soluble fraction of bacterial lysates with glutathione-SEPHAROSE™ beads. The FLAG-tagged SCUBE2-FL, EGF, Spacer, CR, and CUB protein (FLAG.SCUBE2-FL, -EGF, -Spacer, -CR, -CUB) was produced by overexpression from HEK-293T cells. Recombinant VEGF$_{165}$ protein was purchased from R&D Systems. For the SCUBE2 and VEGF$_{165}$ interaction assay, the recombinant VEGF$_{165}$ protein was mixed with FLAG.SCUBE2-FL, EGF, Spacer, CR, and CUB protein bound to anti-FLAG M2 antibody-agarose beads or control beads in 0.5 ml of binding buffer [40 mM HEPES (pH 7.5), 100 mM KCl, 0.1% NONIDET™ P-40, and 20 mM 2-mercaptoethanol]. After incubation for 4 h at 4° C., the beads were washed extensively, and interacting protein was visualized by immunoblotting using anti-VEGF antibody. For the SCUBE2 and VEGFR2 interaction assay, GST-tagged SCUBE2-CUB protein was mixed with Myc.VEGFR2-FL, -D1, -D2 protein in 0.5 ml binding buffer. After incubation for 4 h at 4° C., the protein solutions were incubated with glutathione-SEPHAROSE™ for 2 h with gentle rocking. After three washes with binding buffer, precipitated complexes were visualized by immunoblotting using anti-Myc antibody.

Confocal immunofluorescence microscopy. Endothelial cells were fixed in 4% formaldehyde, blocked with 2% fetal bovine serum for 1 h, and incubated with chicken anti-SCUBE2 and mouse anti-VEGFR2 antibody for 1 h. Slides were washed 3 times with PBS and stained with ALEXA FLUOR® 488-labeled anti-mouse IgG antibody and Alexa Fluor 594-labeled anti-chicken IgG antibody for 1 h, then washed 3 times in PBS and mounted by using VECTASHIELD® mounting medium with DAPI. Fluorescence images were captured at room temperature under a confocal microscope.

RNA Extraction, cDNA Synthesis, and RT-PCR

Total RNA was prepared from cultured cells by the TRIZOL® method. First-strand cDNA synthesis with SUPERSCRIPT™ II reverse transcriptase involved 5 µg RNA. One-tenth of the first-strand cDNA reaction was used for each PCR as a template. The PCR products were run on a 1% agarose gel. Primers are listed in Table 1.

Immunoprecipitation and Western Blot Analysis

The Myc-tagged VEGFR2 expression constructs were transfected alone and in combination with a series of the expression plasmids encoding the indicated FLAG-tagged SCUBE2 protein in HEK-293T cell. Two days after transfection, cells were washed once with PBS and lysed for 5 min on ice in lysis buffer (25 mM Hepes, pH7.6, 150 mM NaCl, 5 mM EDTA, 10 µg/ml aprotinin, 5 µg/ml leupeptin, 10% glycerol, and 1% TRITON® X-100). Cell lysates were clarified by centrifugation at 10,000×g for 20 min at 4° C. Samples were incubated with 1 µg of the indicated antibody and 20 µl of 50% (v/v) Protein A-agarose for 2 h with gentle rocking. After 3 washes with lysis buffer, precipitated complexes were solubilized by boiling in Laemmli sample buffer, fractionated by SDS-PAGE, and transferred to PVDF membranes, which were blocked with phosphate buffered saline (pH 7.5) containing 0.1% gelatin and 0.05% TWEEN® 20 and blotted with the indicated antibodies. After 2 washes, the blots were incubated with horseradish peroxidase-conjugated goat anti-mouse IgG for 1 h. After washing the membranes, the reactive bands were visualized by use of the VISGLOW™ chemiluminescent substrate, HRP system (Visual Protein).

Statistical analysis. Data are presented as mean±SD and were analyzed by two-tailed paired t test. P<0.05 was considered statistically significant.

Table 1 lists primer sequences and SEQ ID NO: for RT-PCR (SEQ ID NOs: 69-82; 85-86); for ChIP (SEQ ID NOs: 83-84); for Q-PCR (SEQ ID NOs: 87-94): for genotyping (SEQ ID NOs: 95-102).

TABLE 1

| Gene | Forward (SEQ ID NO:) | Reverse (SEQ ID NO:) |
|---|---|---|
| SCUBE1 | TGCGGCGGCGAGCTTGGTGAC (69) | TTTGGAGCGCAGCAGTTTGATGAA (70) |
| SCUBE2 | TCTTGCCCAGGAAATACTACGACT (71) | TGGGCCAGGACATCAAACAGAG (72) |
| SCUBE3 | TGGCCCAATGCAAGAATCGTCAGT (73) | TGGGCTAGCACCTCAAAGAAG (74) |
| GAPDH | GCCAAAAGGGTCATCATCTC (75) | ACCACCTGGTGCTCAGTGTA (76) |
| Scube1 | CGGCGGCGAACTTGGTGACTACA (77) | TTGATAAAGGACCGGGGGAACAT (78) |
| Scube2 | TGACTACCTGGTGATGCGGAAAAC (79) | CAGTGGCGTGTGGGAAGAGTCA (80) |
| Scube3 | TGCTCCCCGGGCCACTACTAT (81) | AGCGCTGTTGGCCTCACTGGTCTT (82) |
| SCUBE2 | GCACACGCACGCGCGCACACA (83) | GAAGGGTGCAGAGGGTGTGCT (84) |
| Gapdh | ATCATCCCTGCATCCACTGGTGCTG (85) | TGATGGCATTCAAGAGAGTAGGGAG (86) |
| SCUBE1 | AACATCCCGGGGAACTACAG (87) | GCAGCCACCATTATTGTCCT (88) |
| SCUBE2 | CAGGCAGAGTCCTGTGGAGT (89) | TAAAATGCAGCGTTCTCGTG (90) |
| SCUBE3 | CCTGCTTGTCCTGCTGGT (91) | TCGATGTGGCAGTIGTCAGT (92) |

TABLE 1-continued

| Gene | Forward (SEQ ID NO:) | Reverse (SEQ ID NO:) |
|---|---|---|
| GAPDH | TGAAGGTCGGAGTCAACGG (93) | AGAGTTAAAAGCAGCCCTGGTG (94) |
| Scube2-5'Flox | ATAGTCGACTGTTGTCCAGTATCTGTTGC (95) | ATAGCGGCCGCTACGACACCCTGGGATAAAG (96) |
| Scube2-3'Flox | GGCCATGTCCCTGAAGAAAACTA (97) | TTATGGGGCCAAGACACTCAAA (98) |
| Scube2-Null | CTGGGGCCTCTGGGACACTATT (99) | GTTATGGGGCCAAGACACTCAAA (100) |
| Cre | TTACCGGTCGATGCAACGAGTGATG (101) | GTGAAACAGCATTGCTGTCACTT (102) |

SCUBE1-3 and GAPDH are human genes; Seube1-3 and Gapdh are mouse genes.

Results

SCUBE2 is Expressed in Human ECs and Regulates VEGF-Induced EC Proliferation and Tube Formation We first confirmed SCUBE2 protein expression in HUVECs by immunostaining (FIG. 1A), flow cytometry (FIG. 1B), and western blot analysis (FIG. 1C). Confocal immunofluorescence staining and flow cytometry revealed SCUBE2 localized partially on the EC membrane (FIGS. 1A and 1B). In addition, protein levels were higher in proliferating, sub-confluent ECs than growth-arrested, confluent ECs (FIG. 1C).

We then investigated a potential role for SCUBE2 in regulating VEGF responses by overexpressing and knocking down SCUBE2 in human ECs. After transduction of recombinant lentivirus encoding the full-length FLAG-tagged SCUBE2 or two independent SCUBE2-targeting short hairpin RNAs (shRNA #1 and #2) in HUVECs, the overexpression and knockdown of SCUBE2 were verified by RT-PCR or western blot analyses (FIGS. 1D and 1G). SCUBE2 overexpression significantly increased (FIGS. 1E and 1F) and SCUBE2 knockdown (FIGS. 1H and 1I) markedly reduced VEGF-induced EC growth and capillary-like network formation on MATRIGEL™. Together, these data support a role for SCUBE2 in modulating VEGF-induced proliferation and tubulogenesis in HUVECs.

Upregulation of SCUBE2 by HIF-1α in HUVECs

Figure 2:
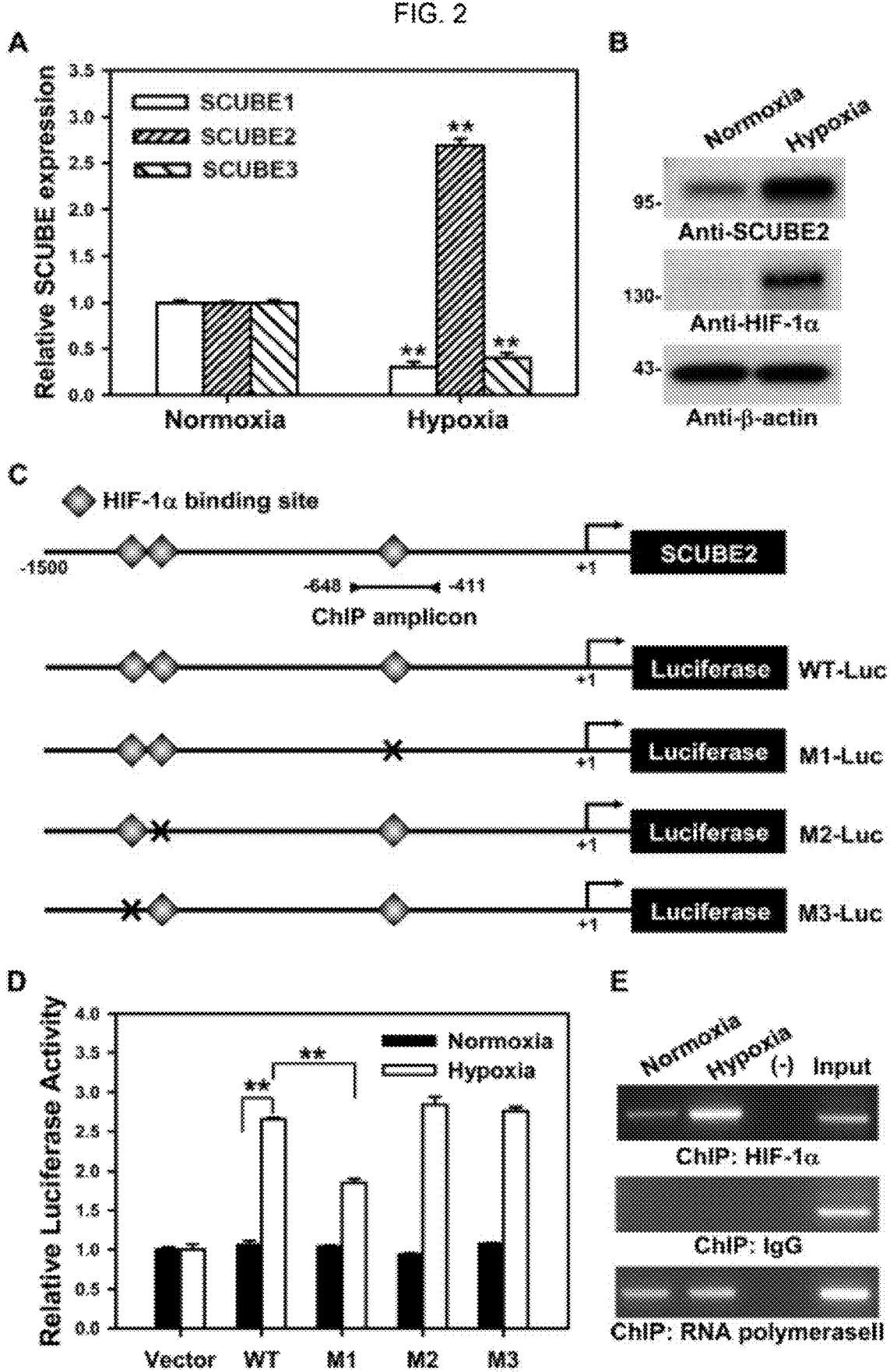
FIG. 2 shows hypoxia mediated HF-1α-induced upregulation of SCUBE2 in HUVECs. A and B, SCUBE2 was upregulated in HUVECs in response to hypoxia. HUVECs were cultured under normoxia or hypoxia (I %) for 12 hr. Expression of SCUBE2 at both mRNA and protein levels verified by quantitative RT-PCR (A) and western blot (B) analyses. Data are mean t SD from 3 independent experiments. . P<0.01 compared to normoxia. C. Scheme of the SCUBE2 promoter reporter constructs containing the native (WT) or mutated (M1, M2, and M3) HIF-1α binding sites. The location of promoter (−150~+1) of SCUBE2 gene is shown by a lateral line. The HIF-1α-binding sites are marked by diamonds, and the mutant sites are shown as "x" marks. The primers and amplicon region used in the ChIP assay are labeled (upper panel). D, HIF-1α transactivates SCUBE2 promoter-driven luciferase activity. Quantification of activity of SCUBE2 WT or mutated promoter constructs transiently transfected into HUVECs. Luciferase activity was normalized to Renilla luciferase activity (pRL-TK) to control for transfection efficiency. E, HIF-1a directly binds to the SCUBE2 promoter with hypoxia. ChIP assay of in vivo binding of HIF-1α protein to the promoter of SCUBE2 in HUVECs analyzed by PCR with specific primers for HIF-1α amplifying a 238-bp fragment. Lack of cell lysates (−) was a negative control. Data are mean t SD from 3 independent experiments. , P<0.01.

Because hypoxia-induced VEGF expression by HIF-1α is critical for postnatal neovascularization, we then investigated whether endothelial SCUBE2 is also upregulated by a similar mechanism. After 12-h exposure of HUVECs to hypoxia, the expression of SCUBE2 but not SCUBE1 or SCUBE3 was significantly increased at both mRNA and protein levels, which was concomitant with HIF-1α accumulation (FIGS. 2A and 2B). Furthermore, ChIP assay and promoter mutation analysis confirmed that endogenous HIF-1α could indeed interact with a DNA region that harbors a consensus HIF binding motif (A/GCTGA) within the SCUBE2 promoter and transactivate SCUBE2 expression in HUVECs with hypoxia treatment (FIG. 2C-2E).

Generation of EC-Specific Scube2-Knockout (EC-KO) Mice

To further investigate the role of endothelial Scube2 on VEGF responses in vivo, we knocked out Scube2 specifically in ECs by crossing mice carrying a conditional "Floxed" allele of Scube2 [flanking the exons encoding 9 EGF-like repeats, the spacer region, 3 cysteine-rich motifs, and the CUB domain with loxP] with transgenic mice expressing the bacteriophage recombinase Cre under the control of the angiopoietin receptor (Tie2) promoter, which is pan-endothelial expressed. Male Tie2-Cre: Scube2$^{+/-}$ were bred to female Scube2$^{Flox/Flox}$ mice to obtain Tie2-Cre; Scube2$^{Flox/+}$ (designated "control") and Tie2-Cre: Scube2$^{Flox/-}$ (designated EC-KO) mice.

To determine the endothelial-specific recombination efficiency of the Scube2$^{Flox}$ allele, primary lung MLECs were isolated from control and EC-KO mice. Flow cytometry revealed these cell populations highly enriched in ECs because approximately 95% of these cells expressed CD31. In addition, both mRNA and protein levels of Scube2 were efficiently and specifically ablated without obvious compensatory upregulation of Scube1 and Scube3 in EC-KO MLECs. Consistently, immunostaining of adult mouse lungs verified the complete abrogation of endothelial (but not bronchial epithelial) Scube2 expression in EC-KO mice. Therefore. Scube2 was efficiently ablated in the endothelial compartment of adult EC-KO mice.

Control and EC-KO mice were recovered at the expected Mendelian ratio and showed the normal pattern of weight gain, so vasculogenesis and angiogenesis were sufficient for normal development. We observed no phenotypic differences in general health and behavior between control and EC-KO animals. EC-KO females reproduced normally and had normal litter sizes, which suggested sufficient reproductive angiogenesis to allow for colony propagation. Together, these data suggest that physiological angiogenesis was grossly unaffected by endothelial inactivation of Scube2.

Figure 3:
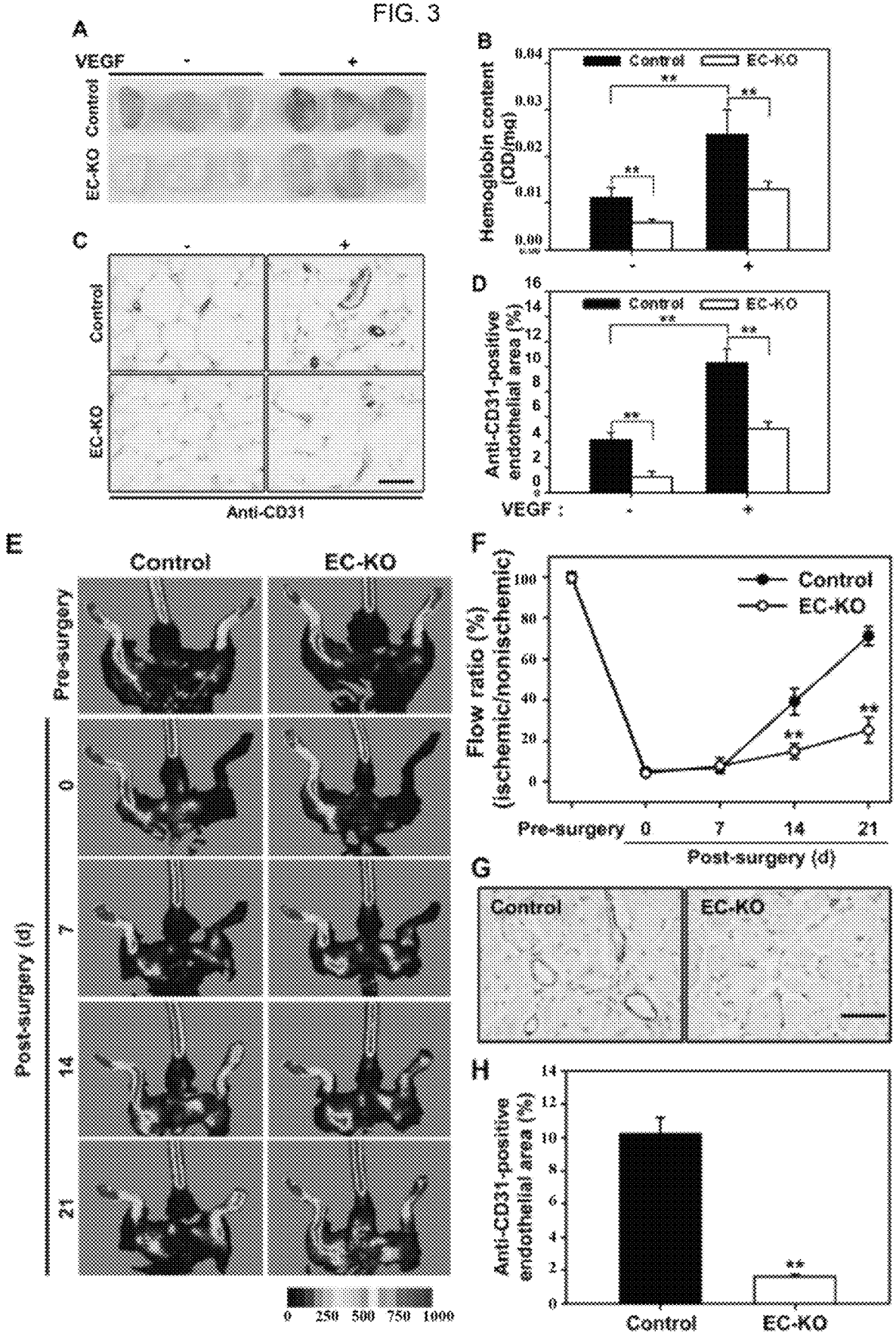
FIG. 3 shows attenuation of adult angiogenesis of in Scube2 EC-KO mice. A-D, MATRIGEL™ plug assays. Representative photographs of MATRIGEL™ plugs containing saline (−) or VEGF (+) removed from control and EC-KO mice at 7 d post-injection (A). Hemoglobin content of saline (−) and VEGF (+)-supplemented MATRIGEL™ plugs from control and EC-KO mice (B). Data are mean±SD (n=5). , P<0.01. Anti-CD31 staining of sections of MATRIGEL™ plugs containing saline (−) or VEGF (+) excised from control and EC-KO mice (C). Scale bar=40 μm. Vascularization of MATRIGEL™ plugs as determined by anti-CD31 antibody positivity by using IMAGEJ™ (D). Data are mean±SD (n=5). , P<0.01. E-H, Hind-limb ischemia-induced neovascularization. Representative laser-Doppler images (A) and quantification of hind-limb blood flow (B) before and after right femoral artery ligation in mice. Representative images (C) and quantification of anti-CD31 immunostaining of calf blood vessels (D) at 21 days after femoral artery ligation in control and EC-KO mice. Scale bar=100 μm. Data are mean±SD (n=6). **, P<0.01 compared to control.

Responses to Exogenous VEGF and Adult Angiogenesis are Impaired in Scube2 EC-KO Mice To explore the potential function of endothelial Scube2 in VEGF-stimulated angiogenesis in vivo, we used MATRIGEL™-plug assay with MATRIGEL™ mixed with VEGF (+) or saline (−) administered subcutaneously to age- and sex-matched EC-KO and control mice with recovery 7 days later (FIG. 3). On gross examination, MATRIGEL™ plugs containing VEGF from control mice were reddish-brown (FIG. 3A). However, plugs containing VEGF from EC-KO mice were paler than control plugs (FIG. 3A). Consistently, total hemoglobin content, a measure of intact vessel formation associated with the amount of newly formed capillary network, in VEGF-containing MATRIGEL™ plugs was reduced ~50% for EC-KO mice (FIG. 3B). To ensure that this hemoglobin difference was caused by reduced microvasculature density, blood vessel infiltration in implants was quantified by immunostaining with anti-CD31 antibody (a marker of endothelia) (FIGS. 3C and 3D).

In contrast to MATRIGEL™-implanted control mice, implanted EC-KO mice showed decreased vascularization, even in saline-containing plugs (FIG. 3C). Furthermore, the microvascular density of VEGF-containing plugs was lower by 50% in EC-KO than control mice (FIG. 3D), and no large vascular tubes were seen (FIG. 3C), which suggests that the VEGF-induced adult angiogenic response depends on endothelial Scube2 in vivo.

To further evaluate the proangiogenic effect of endothelial Scube2, we used a second adult neovascularization model (i.e., hind-limb ischemia): the common femoral artery was ligated in control and EC-KO mice and blood flow as well as vascular regeneration and angiogenesis were monitored over time by laser Doppler imaging and anti-CD31 immunostaining, respectively. Laser-Doppler analyses revealed a similar degree of reduced blood flow in ligated limbs of control and EC-KO animals after surgery as compared with nonligated contralateral limbs (FIGS. 3E and 3F), which indicates comparable post-surgery ischemia in both strains. In control mice, blood flow recovered to almost baseline levels by 21 days after surgery. However, blood flow recovery was significantly impaired in EC-KO animals (FIGS. 3E and 3F). Consistently, histology of the gastrocnemius (calf) muscle showed lower anti-CD31-positive capillary density induced by ligation in EC-KO than control mice at 21 days (FIGS. 3G and 3H). Therefore, functional Scube2 may be required in the endothelium for revascularization after ischemia induced by femoral artery ligation.

SCUBE2 Co-Localizes and Interacts with VEGFR2 and Potentiates VEGF Binding to VEGFR2 in HUVECs Because SCUBE2 can regulate VEGF responses both in vitro and in vivo (FIGS. 1 and 3) and SCUBE proteins can function as co-receptors for signaling receptor serine/threonine kinases or RTKs, we examined whether SCUBE2 co-localizes and interacts with VEGFR2 in HUVECs. Confocal microscopy and co-immunoprecipitation experiments indeed revealed that VEGF promotes their co-localization at the plasma membrane and enhances the association of SCUBE2 with VEGFR2, peaking at 10 min after VEGF stimulation in HUVECs. This result was further elaborated in HEK-293T cells transfected with SCUBE2 and VEGFR2 expression plasmids, showing that the CUB domain of SCUBE2 can interact with the extracellular immunoglobin-like folds of VEGFR2. In addition, this SCUBE2-VEGFR2 interaction appeared specific because anti-SCUBE2 immunoprecipitation did not pull down other RTKs such as VEGFR1 and EGFR or another VEGFR2 co-receptor Neuropilin-1. Most importantly, besides binding to VEGFR2, SCUBE2 could directly bind to VEGF-$A_{165}$ via its EGF-like repeats. We have performed additional co-immunoprecipitation experiments to verify whether SCUBE1 or SCUBE3 can also bind to VEGF or VEGFR2. Unlike SCUBE2 that can specifically bind to VEGF, SCUBE1 and SCUBE3 cannot interact with VEGF, suggesting that SCUBE1 or SCUBE3 may not function as a co-receptor for VEGF (See Lin et al. "Endothelial SCUBE2 Interacts With VEGFR2 and Regulates VEGF-Induced Angiogenesis" *Arterioscler Thromb Vase Biol.* 2017; 37:144-155).

To evaluate whether SCUBE2 could indeed increase VEGF binding to VEGFR2, we first produced a functional alkaline phosphatase (AP)-VEGF fusion protein as described. As compared with control AP protein, AP-VEGF protein showed binding on HUVECs endogenously expressing VEGFR2. Interestingly, SCUBE2 overexpression increased and SCUBE2 knockdown or genetic knockout decreased AP-VEGF binding as compared with corresponding control HUVECs. Consistently, Scatchard analysis showed that the binding affinity of VEGF to VEGFR2 was greater by a factor of ~3 with VEGFR2 co-expressed with SCUBE2 than with VEGFR2 alone in HEK-293T cells ($K_d$=0.21 vs 0.58 nM). Together, these data suggest that SCUBE2 acts as a co-receptor for VEGFR2 and potentiates VEGF binding to VEGFR2.

Figure 4:
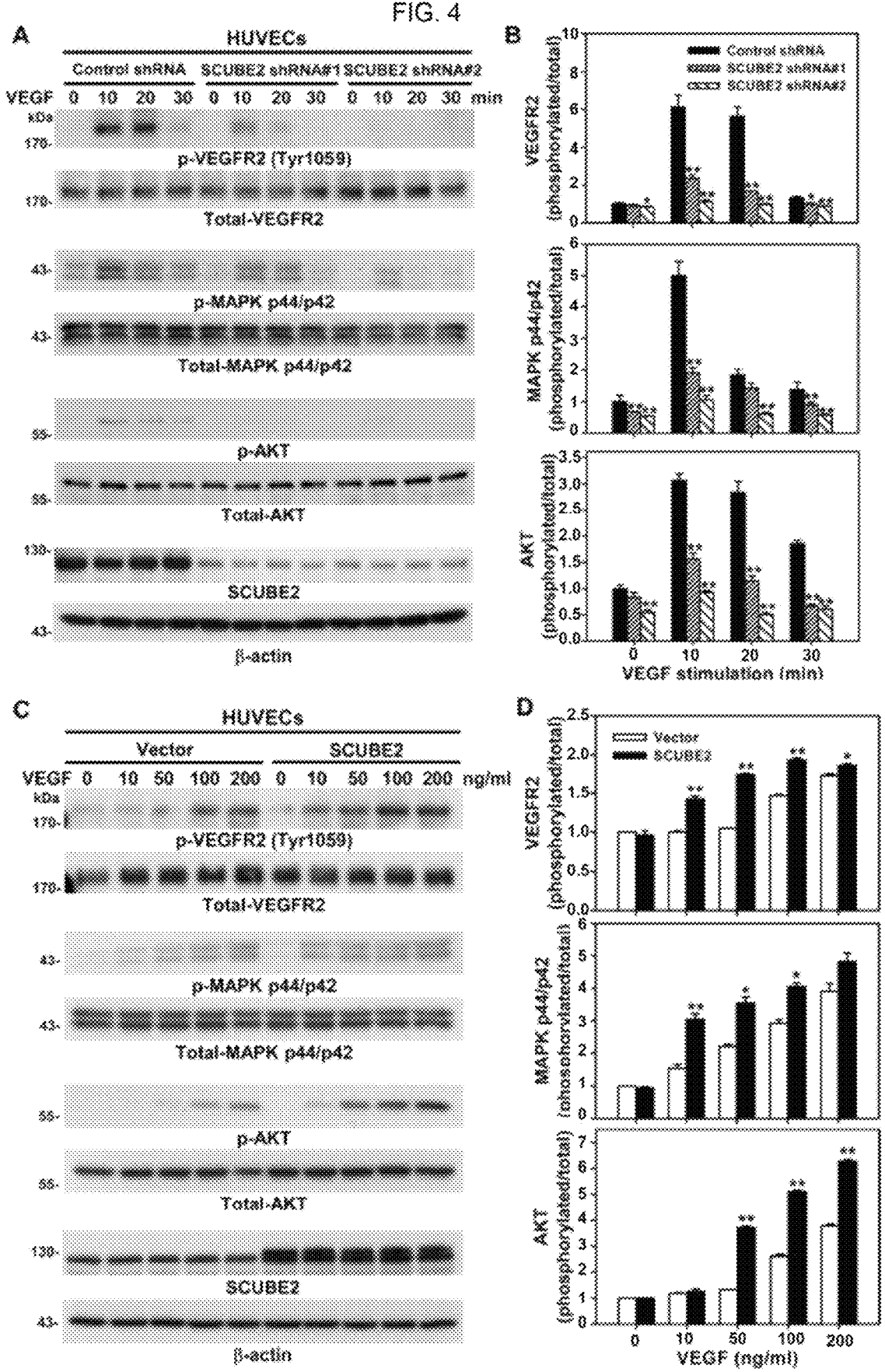
FIG. 4 shows that SCUBE2 modulates VEGFR2 phosphorylation and downstream signaling in HUVECs. A and B. SCUBE2 knockdown impairs VEGF signaling in HUVECs. Western blot analysis of VEGF signaling in HUVECs (A) and quantification (B) of VEGF-induced phosphorylation of VEGFR2 at Tyr1059, p44/42 mitogen-activated protein kinase (MAPK) at Thr202/Tyr204 and AKT at Ser473 with control and SCUBE2 shRNA knockdown in HUVECs. Data are mean±SD from 3 independent experiments. *, P<0.05; **, P<0.01 compared to control. C and D. Western blot analysis of VEGF signaling in ECs (C) and quantification (D) of VEGF-induced phosphorylation of VEGFR2 Tyr1059, p44/42 MAPK Thr202/Tyr204, and AKT Ser473 in control and SCUBE2-overexpressing ECs. Data are mean±SD from 3 independent experiments. *, P<0.05; **P<0.01 compared to vector.

SCUBE2 Modulates VEGFR2 Phosphorylation and Downstream Signaling in HUVECs We next investigated whether SCUBE2 facilitates VEGF-activation signals in HUVECs. To this end, we used VEGF as a stimulator and SCUBE2 shRNA knockdown or SCUBE2 overexpression to evaluate the function of SCUBE2 on VEGF-induced signaling. VEGF could induce VEGFR2 Tyr1059 phosphorylation, the p44/42 MAPK signaling cascade, and AKT activation. However, SCUBE2 shRNA knockdown reduced (FIGS. 4A-B) and SCUBE2 overexpression (FIGS. 4C-D) enhanced VEGF-induced VEGFR2 phosphorylation, the p44/42 MAPK signaling cascade, and AKT activation. Our data strongly indicate that as a VEGFR2 co-receptor, SCUBE2 is involved in regulating VEGF-induced VEGFR2 downstream signals in HUVECs. We have determined the phosphorylation status of SCUBE2 upon treatment of VEGF in HUVECs. After VEGF stimulation, anti-SCUBE2 immunoprecipitates were blotted with anti-phosphotyrosine (p-Tyr) or anti-phosphoserine/threonine (p-Ser/Thr) pan-specific antibody, respectively. SCUBE2 appears unphosphorylated upon treatment with VEGF up to 30 min. However, further phospho-proteomic analysis will be needed to verify whether or not SCUBE2 is phosphorylated after VEGF stimulation.

Scube2 Modulates VEGF Signaling in Primary Murine Lung ECs (MLECs)

Figure 5:
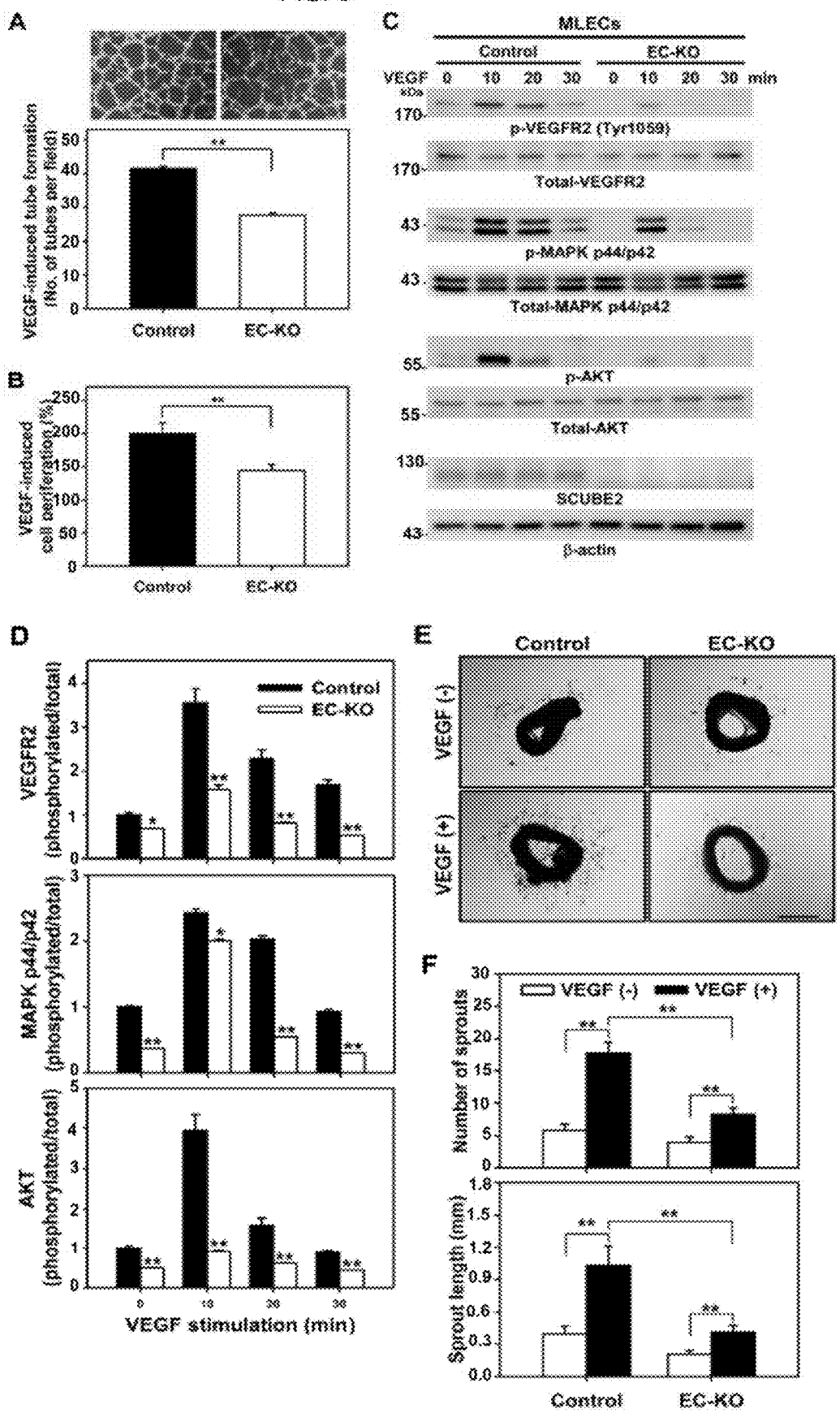
FIG. 5 shows attenuation of VEGF responses and signaling in EC-KO mouse lung ECs (MLECs). A and B, VEGF-stimulated tubulogenesis (A) and proliferation (B) of EC-KO MLECs. Data are meant SD from 3 independent experiments. **, P<0.01 compared to control. C and D, Western blot analysis of VEGF signaling in MLECs (C) and quantification (D) of VEGF-induced phosphorylation of VEGFR2 Tyr1059, p44/42 MAPK Thr202:Tyr204, and AKT Ser473 in control and EC-KO MLECs. Data are mean±SD from 3 independent experiments. *, P<0.05; **, P<0.01 compared to control. E, Photomicrographs show the angiogenic response of 5 day culture collagen-embedded thoracic aorta ring explants from control and EC-KO mice. Scale bar=1 mm. F, Quantification of the number and length of microvessel sprouts. The angiogenic response was determined for each individual aortic ring explant by quantifying the number of growing microvessels (left) and by measuring the total length occupied by the newly formed microvessels (right).

Similar to our knockdown experiments in HUVECs (FIGS. 1G-1I), VEGF-induced cell proliferation and tube formation were markedly attenuated in EC-KO MLECs as compared with control MLECs (FIGS. 5A-B). We further assessed the effect of endothelial Scube2 gene deletion on VEGF-induced signaling. We stimulated control and EC-KO MLECs with 50 ng % ml VEGF for 0, 10, 20, and 30 min. In agreement with SCUBE2 shRNA knockdown in HUVECs, VEGF signaling, determined by phosphorylation of VEGFR2, p44/42 MAPK, and AKT, was markedly lower in EC-KO than control MLECs (FIGS. 5C-D).

Decreased Microvessel Outgrowth from Aortic Explant of Scube2 EC-KO Mice

We further investigate the role of SCUBE2 in angiogenesis using the ex vivo aortic ring sporting assay, in which we compared the angiogenic potential of aortic fragments derived from control and EC-KO mice. The aortic rings, isolated from control and EC-KO mice, were treated with PBS or VEGF, and the angiogenic response was determined for each individual aortic ring explant by quantifying the number of growing microvessels and by measuring the total length occupied by the newly formed microvessels. Quantification of the number of the tube-like structures (sprouts) and of the length of sprouts in response to VEGF (30 ng/ml) at 5 days, showed a significant decrease of both parameters in EC-KO compared to control aortic rings (FIGS. 5E-5F). Therefore, these ex vivo results confirm in vitro data and support the role of SCUBE2 in VEGFR2-mediated angiogenesis.

Tumor Growth is Reduced in EC-KO Mice

Figure 6:
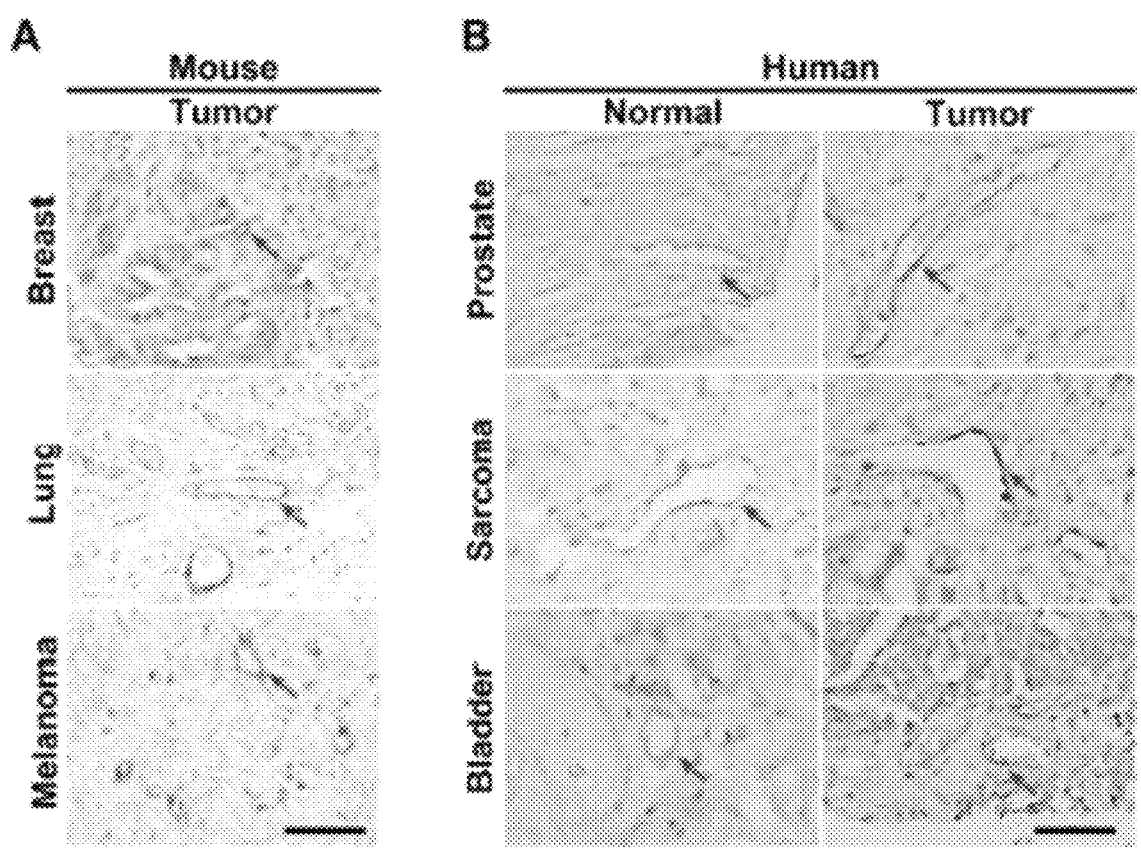
FIG. 6 shows that SCUBE2 is highly expressed in tumor endothelial cells (ECs). Immunohistochemistry of enriched EC expression of SCUBE2 (brown color indicated by red arrows) in mouse (breast, lung, melanoma) (A) and human (prostate, sarcoma, bladder) (B) carcinomas. The transgenic mouse mammary tumor virus polyoma middle T (MMTV-PyMT) model was used to obtain spontaneous mouse breast tumors derived from lung metastases. In addition, two xenograft tumors were developed by subcutaneous injection of syngeneic melanoma (B16F10) or Lewis lung carcinoma (LLC) cells. Endothelial immunoreactivity was developed as red color (instead of brown) in melanoma tumor because of the melanin background of melanoma cells. Human normal and tumor pairs were purchased from a commercial tissue microarray source.
Figure 7:
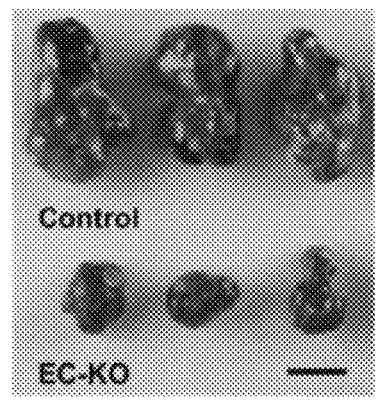
FIG. 7 shows that loss of endothelial Scube2 retards tumor angiogenesis and tumor growth in EC-KO mice. A-D, Control and EC-KO mice were subcutaneously injected with B16F10 melanoma cells or Lewis lung carcinoma (LLC) tumor cells. Representative photos of B16F10 (A) and LLC (B) tumors at 16 d post-implantation and rate of tumor growth measured at the indicated time (C and D). Scale bar=10 mm. E-H, Impaired tumor microvasculature in EC-KO mice. Anti-CD31 staining of tumor sections showing decreased number of ECs and vessel structures in EC-KO mice (E and F). Quantification of tumor vascularization 16 d after implantation of tumor cells (G and H). Scale bar=40 μm. Data are mean±SD (n=6). **, P<0.01.
Figure 7:
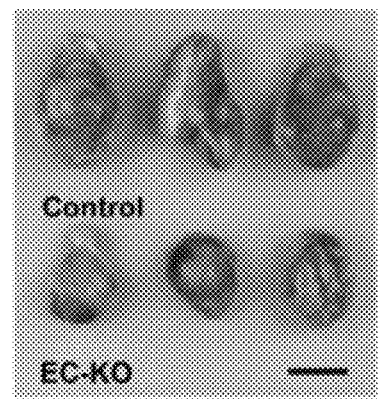
Figure 7:
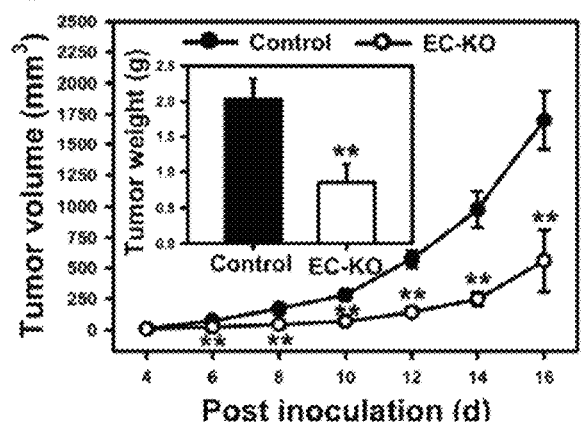
Figure 7:
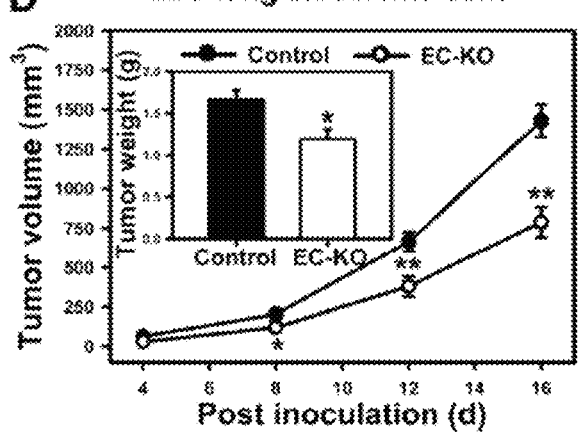
Figure 7:
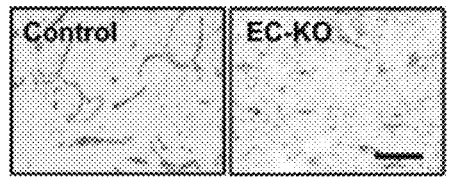
Figure 7:
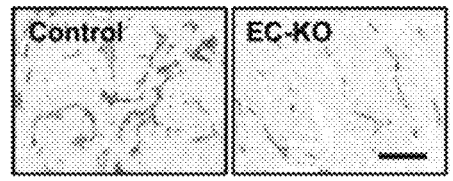
Figure 7:
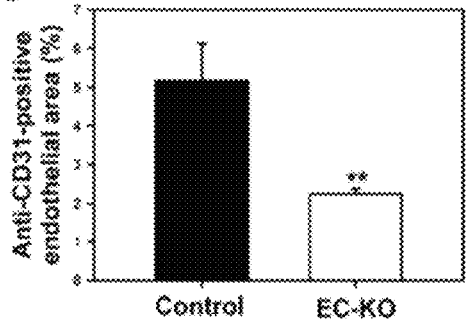
Figure 7:
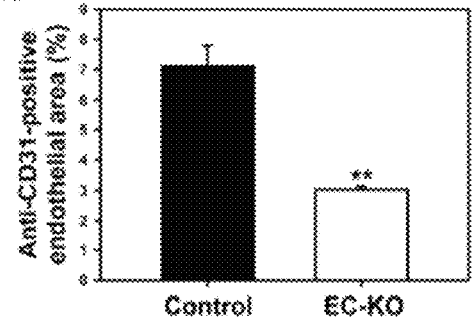

SCUBE2 is highly expressed in tumor endothelial cells. FIG. 6 shows the results of immunohistochemistry, illustrating enriched EC expression of SCUBE2 (arrows) in breast, lung, melanoma (A) and prostate, sarcoma, and bladder carcinomas (B). Given the essential role of endothelial Scube2 in adult neoangiogenesis (FIG. 3), we then studied the effect of endothelial inactivation of Scube2 (EC-KO) on pathological tumor angiogenesis and tumor growth. Control and EC-KO mice were injected subcutaneously with syngeneic melanoma (B16F10) or Lewis lung carcinoma (LLC) cells. Both the growth and size of tumors were lower for EC-KO than control mice (FIGS. 7A-D). In line with adult angiogenesis defects with the endothelial loss of Scube2, microvascular density (seen by anti-CD31 staining) was markedly lower in EC-KO than control tumors (FIGS. 7E-H), which suggests that endothelial Scube2 plays an essential role in promoting tumor angiogenesis and growth. Importantly, vessel density in nontumorous adult skin was comparable between control and EC-KO animals (data not shown).

Figure 8:
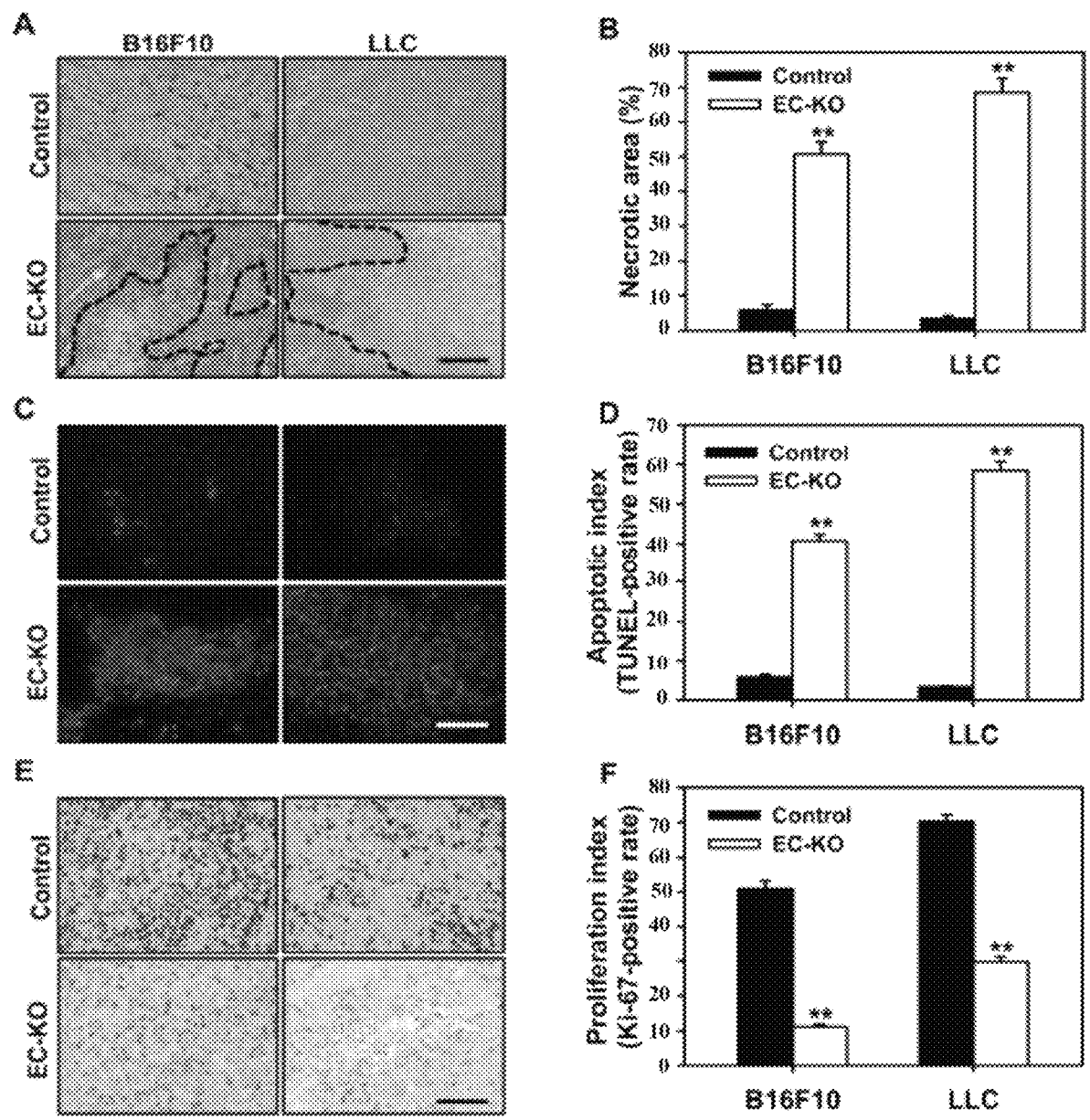
FIG. 8 shows that EC-KO tumors are deprived of oxygen and nutrients and thus undergo apoptosis. H&E staining (A), TUNEL assay (C), and Ki-67 staining (E) in B16F10- or LLC-induced tumor sections from control or EC-KO mice. Quantification of tumor necrosis (B), tumor-cell apoptosis (D) and proliferation (F). Scale bar:=100 μm. Data are mean t SD (n=6). **, P<0.01.

The angiogenesis defects observed in EC-KO mice implied that tumor cells might be deprived of nutrients and oxygen and therefore undergo apoptosis and necrosis. Consistent with this notion, hematoxylin and eosin staining revealed a central core of necrotic tissue in EC-KO tumors but a much smaller necrotic area in control tumors (FIGS. 8A-B). Furthermore, terminal deoxynucleotidyl transferase dUTP nick end labeling (TUNEL) assay and Ki-67 immunostaining showed greater apoptosis and markedly reduced proliferation of tumor cells in EC-KO tumors as compared with control tumors (FIGS. 8C-F). Again, these results indicate that endothelial Scube2 is indispensable for angiogenesis to sustain the survival of tumor cells.

Figure 9:
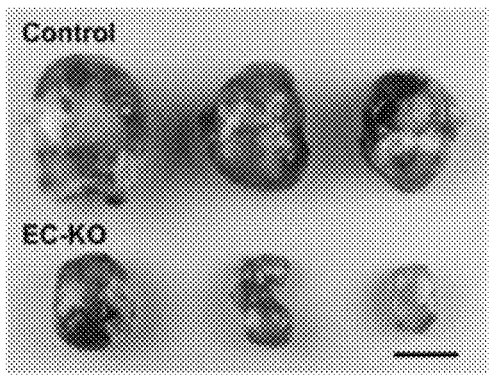
FIG. 9 shows loss of endothelial. Scube2 retards tumor angiogenesis and tumor growth in EC-KO mice. A and B, Control and EC-KO mice were subcutaneously injected with MLTC leydig tumor cells. Representative photos of MLTC Leydig tumors at 60 d post-implantation (A) and rate of tumor growth measured at the indicated time (B). Scale bar=10 mm. C and D, Anti-CD31 staining of tumor sections showing decreased number of ECs and vessel structures in EC-KO mice (C). Quantification of tumor vascularization 16 d after implantation of tumor cells (D). Scale bar=40 μm. Data are mean±SD (n=6). **, P<0.01.
Figure 9:
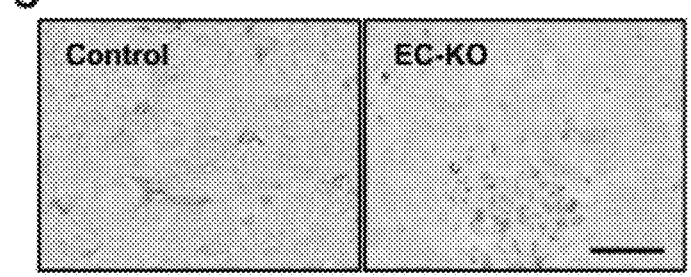
Figure 9:
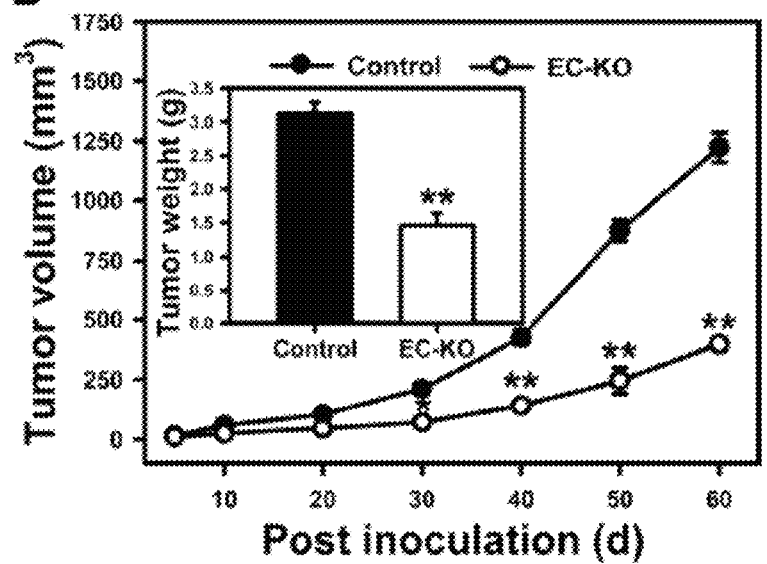
Figure 9:
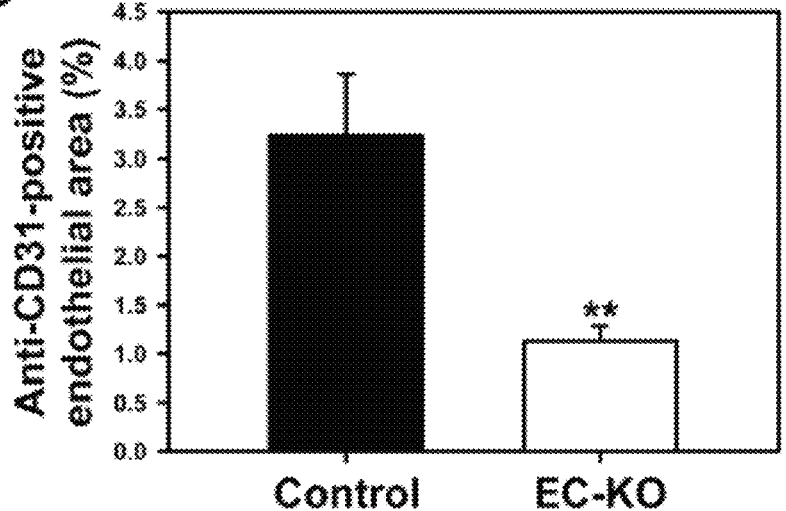

FIG. 9 shows loss of endothelial Scube2 retards tumor angiogenesis and tumor growth in EC-KO mice. Representative photos of MLTC Leydig tumors at 60 d post-implantation and rate of tumor growth measured at the indicated time are shown (A. and B). EC-KO mice showed impaired tumor microvasculature. Anti-CD31 staining of tumor sections showing decreased number of ECs and vessel structures in EC-KO mice (C). Quantification of tumor vascularization 16 d after implantation of tumor cells (D).

Retinal Vasculature Growth is Reduced in EC-KO Mice

Figure 10:
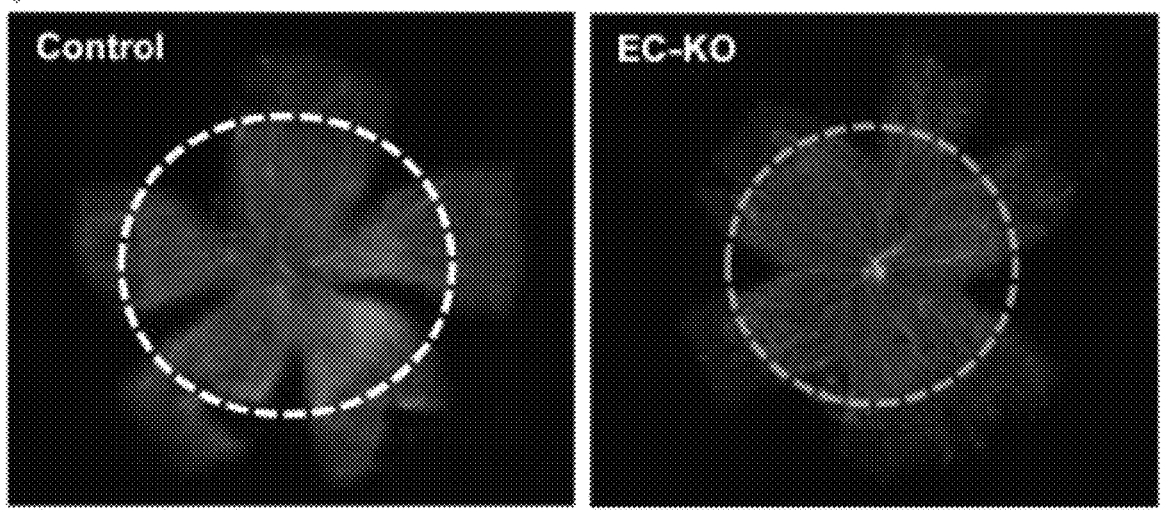
FIG. 10 shows the effect of endothelial ablation of Scube2 on developmental outgrowth of the retinal vasculature. A. Whole-mount P5 retinas from control and EC-KO pups were stained with a pan-endothelial marker CD31. White dashed circle denotes mean control angiogenic front (left) and orange dashed circle mean EC-KO angiogenic front (right). B, High-power magnification (100×) of the angiogenic front. Yellow dots mark filopodia. C and D, Quantification of retinal angiogenesis by measuring radial distance (C) from the optic nerve and number of filopodia (D) (expressed as a percentage of control). Data are mean±SD (n=5 in each group). **P<0.01.
Figure 10:
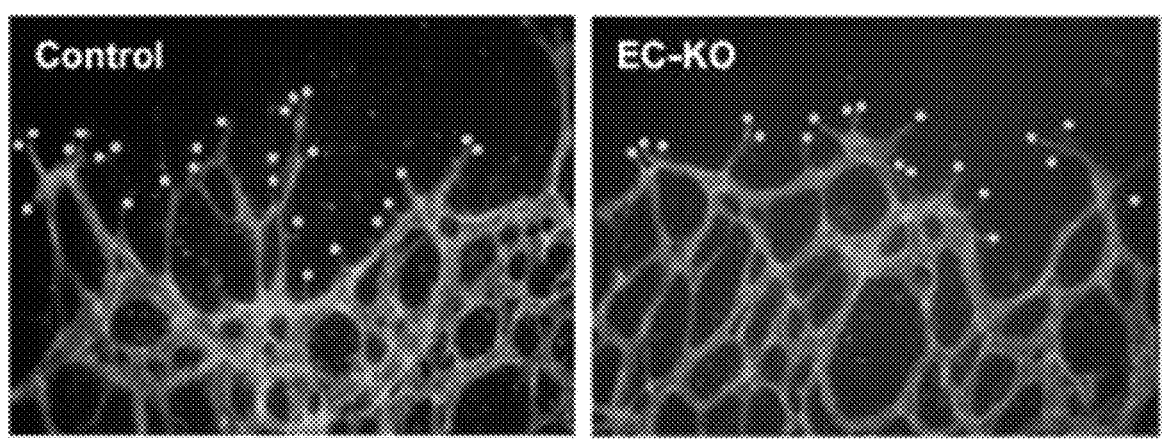
Figure 10:
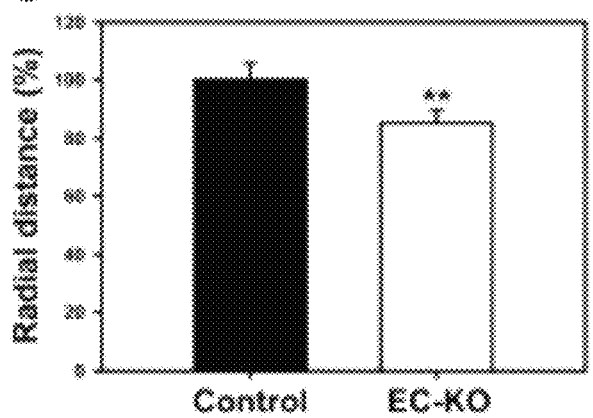
Figure 10:
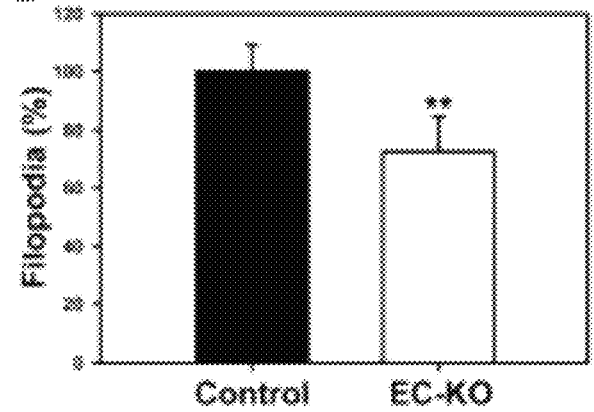

FIG. 10 shows the effect of endothelial ablation of Scube2 on developmental outgrowth of the retinal vasculature.

Oxygen-Induced Retinopathy is Reduced in EC-KO Mice

Figure 11:
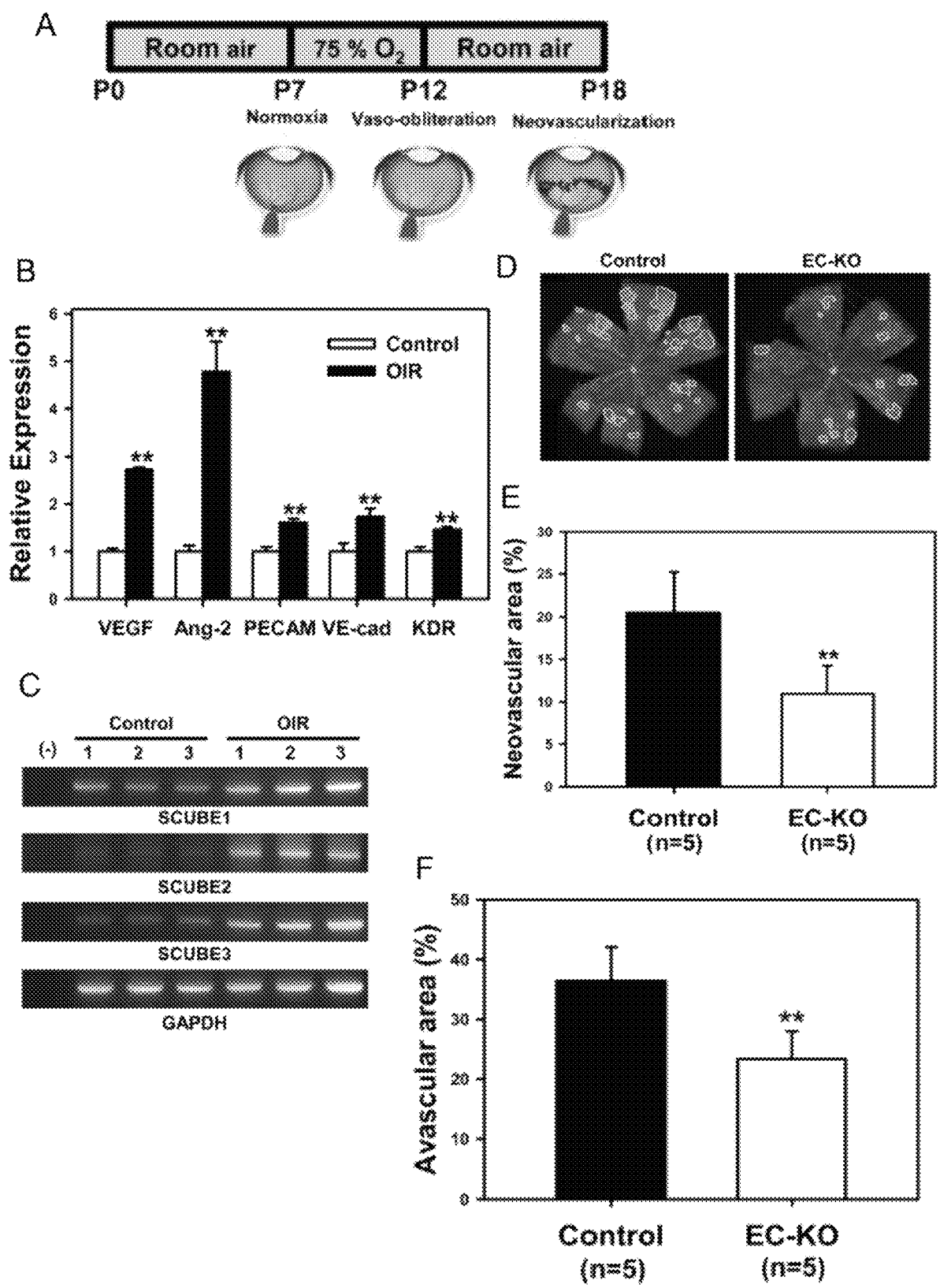
FIG. 11 shows that deletion of SCUBE2 in endothelial cells reduces oxygen-induced retinopathy (OIR). A, Schematic diagram of the OIR model. Neonatal mice were exposed to 75% oxygen from postnatal day (P) 7 to P12 and returned to room air from P12 to P18 to induce maximum pathologic neovascularization at P18. B and C, Total RNAs were isolated from OIR-exposed or age-matched normoxic control mouse retinas at P18 (n:=3) and subsequently applied to Q-PCR or RT-PCR for analyzing the mRNA expression of angiogenesis marker genes (B) or SCUBE gene family (C). D, Whole-mount analysis of the retinal vasculature of conarol or EC-KO mice after exposure to the OIR model. The size of the central avascular area or neovascular area at p18 (6 days after removal from 75% oxygen) is outlined in red or blue, respectively. E and F, Size of the neovascular area (E) or central avascular area (F) relative to that of the entire retina (expressed in %) was significantly smaller in EC-KO mice (n=5) compared to controls (n=5) subjected to the OIR model. **, P<0.01.

FIG. 11 shows that deletion of SCUBE2 in endothelial cells reduces oxygen-induced retinopathy (OIR).

Anti-SCUBE2 Antibodies

SCUBE2 has at least 5 distinct domain motifs (FIG. 12A): an $NH_2$-terminal signal peptide sequence, followed by 9 copies of EGF-like repeats (E), a spacer region, 3 cysteine-rich motifs (Cys-rich), and one CUB domain at the COOH terminus. Amino acids for each domain are (1) SP: a.a. 1-37; (2) EGF-like repeats: a.a. 49-442; (3) Spacer: a.a. 443-669; (4) CR: a.a. 70-803; and (5) CUB: a.a. 838-947. On the basis of domain prediction, mature SCUBE2 protein (a.a. 38 to a.a. 1028) can be secreted into the extracellular medium.

Figure 12:
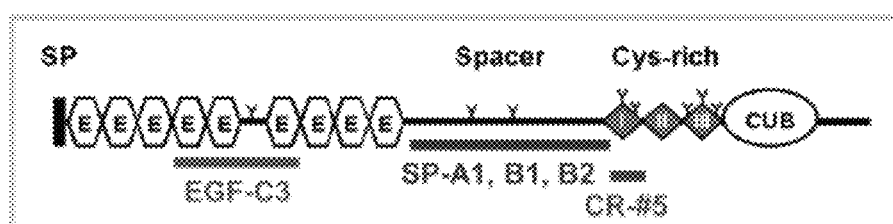
FIG. 12 shows anti-SCUBE2 mAbs with anti-angiogenetic effect. A, Anti-SCUBE2 mAb clones and their targeting domains. B, Anti-SCUBE2 mAbs inhibit vessel angiogenesis by an in vitro tube formation assay. A summary of anti-SCUBE2 mAbs with specificity and anti-angiogenetic effect is shown. h, human; m, mouse: z, zebrafish.
Figure 12:
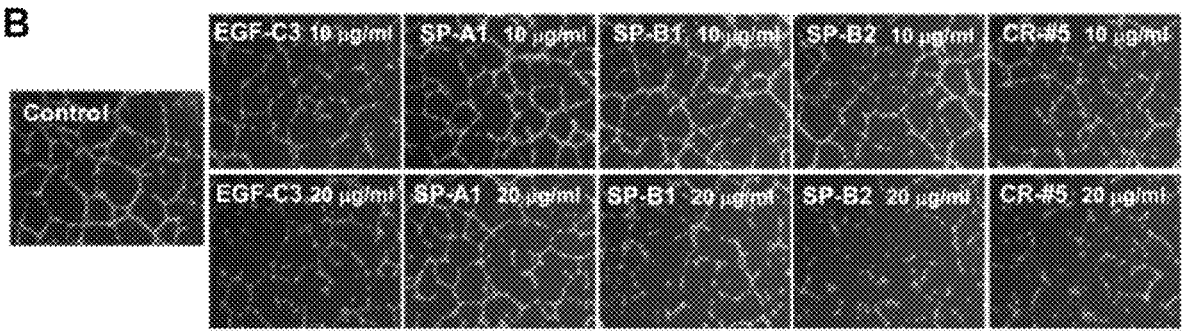

Anti-SCUBE2 antibodies were produced. FIG. 12A shows the specific targeting domain of each anti-SCUBE2 mAb clones. The clone EGF-C3 recognizes the EGF-like repeats 4-6 (a.a. 175-323), whereas SP-A1 (a.a. 441-659), B1 (a.a. 441-659), and B2 (a.a. 441-659) clones bind the spacer region of SCUBE2. The CR-#5 clone detects the 1 cys-rich motif (a.a. 668-725) of SCUBE2. The EGF-C3 clone was obtained by immunized with a recombinant protein containing the EGF-like repeats of SCUBE2 and the SP-A1, B1 and B2 clones was obtained by immunized with a recombinant protein containing the spacer region of SCUBE2. Likewise, the CR-#5 clone was obtained by immunized with a recombinant protein containing the $1^{st}$ cys-rich motif.

These antibodies showed inhibitory activities on vessel tube formation when incubated with endothelial cells in an in vitro tubulogenesis assay (FIG. 12B). The species specificity and anti-angiogenetic activity of these anti-SCUBE2 mAb clones are shown (FIG. 12B). Tables 2-6 show the CDR sequences of anti-SCUBE2 monoclonal antibodies. Complementarity-determining regions 1-3 (CDR1-3), and framework regions 1-4 (FW1-4) for both the $V_H$ and $V_L$ domains are shown.

Treatment of Neovascular Eye Diseases

Figure 13:
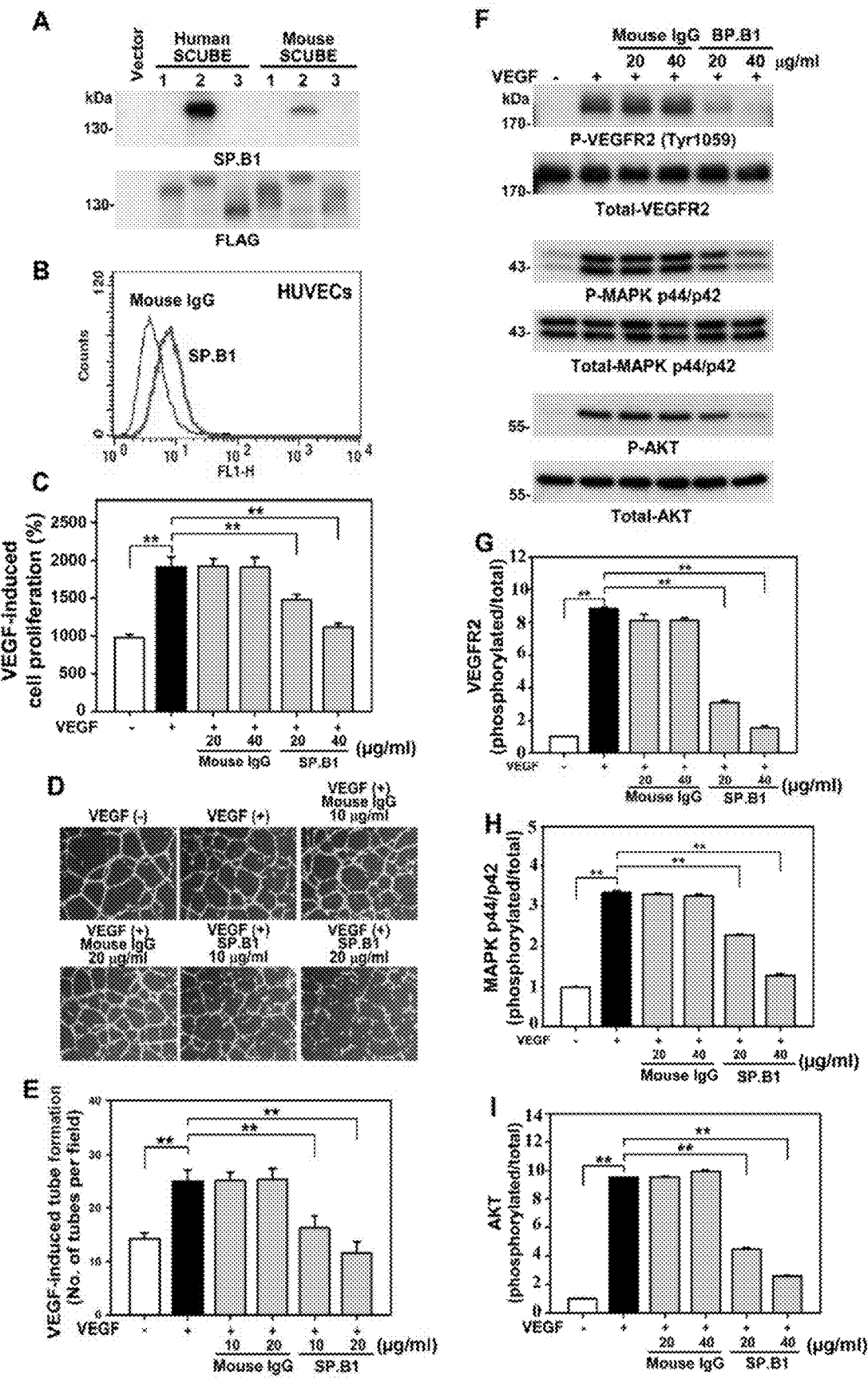
FIG. 13 shows that the anti-SCUBE2 mAb SP.B1 inhibits VEGF-induced responses and signal transduction in HUVECs. A and B, Characterization of anti-SCUBE2 mAb SP.B1. Western blot analysis and flow cytometry of mAb SP.B1 recognizing human and mouse recombinant SCUBE2, not 1 and 3 protein expressed in HEK-293T cells (A) and cell surface expression of SCUBE2 on HUVECs (B). C-I, The mAb SP.B1 blocks VEGF-stimulated cell responses and VEGF-induced VEGFR2 phosphorylation and MAPK/Akt activation. Addition of SP.B1 but not control IgG dose-dependently suppresses VEGF-induced HUVEC proliferation (C) and angiogenesis (D and E). Phosphorylated and total VEGFR2, MAPK, and Akt induced by VEGF in HUVECs with SP.B1 or control IgG (F) and quantification (G-I). Data are mean±SD from 3 independent experiments (G-1). **, P<0.01.

The effect of intravitreal injection of anti-SCUBE2 antibodies on retinal neovascularization is examined in a murine model of oxygen-induced retinopathy. Our preliminary data showed that these anti-SCUBE2 antibodies could suppress the vessel angiogenesis by an in vitro endothelial cell tube formation assay. For example, the SP.B1 clone is capable of inhibiting endothelial cell proliferation and capillary tube formation stimulated by VEGF (FIG. 13C-E).

Anti-SCUBE2 (SP.B1) and Anti-VEGF (Bevacizumab) Synergistically Inhibit Lung, Pancreatic, and Colorectal Carcinoma Growth Because our results suggested that the membrane-associated SCUBE2 plays critical roles in tumor angiogenesis, we evaluated whether inhibition of SCUBE2 by a neutralizing mAb could be a potential agent for treating solid tumors. A mAb specific for SCUBE2 (clone SP.B1) was developed; the mAb did not crossreact with SCUBE1 or 3 (FIGS. 13A-B), which indicates lack of significant off-target effects. Given the proangiogenic activity of SCUBE2, we first assessed the in vitro effects of this mAb in VEGF-stimulated responses in HUVECs. Incubation of SP.B1 mAb but not control IgG blocked VEGF-induced signals, including VEGFR2 phosphorylation and p44/42 MAPK/Akt activation (FIGS. 13F-I). The functional activity of this mAb was verified by its specific ability to inhibit EC proliferation and capillary tube formation stimulated by VEGF (FIGS. 13C-E).

Figure 14:
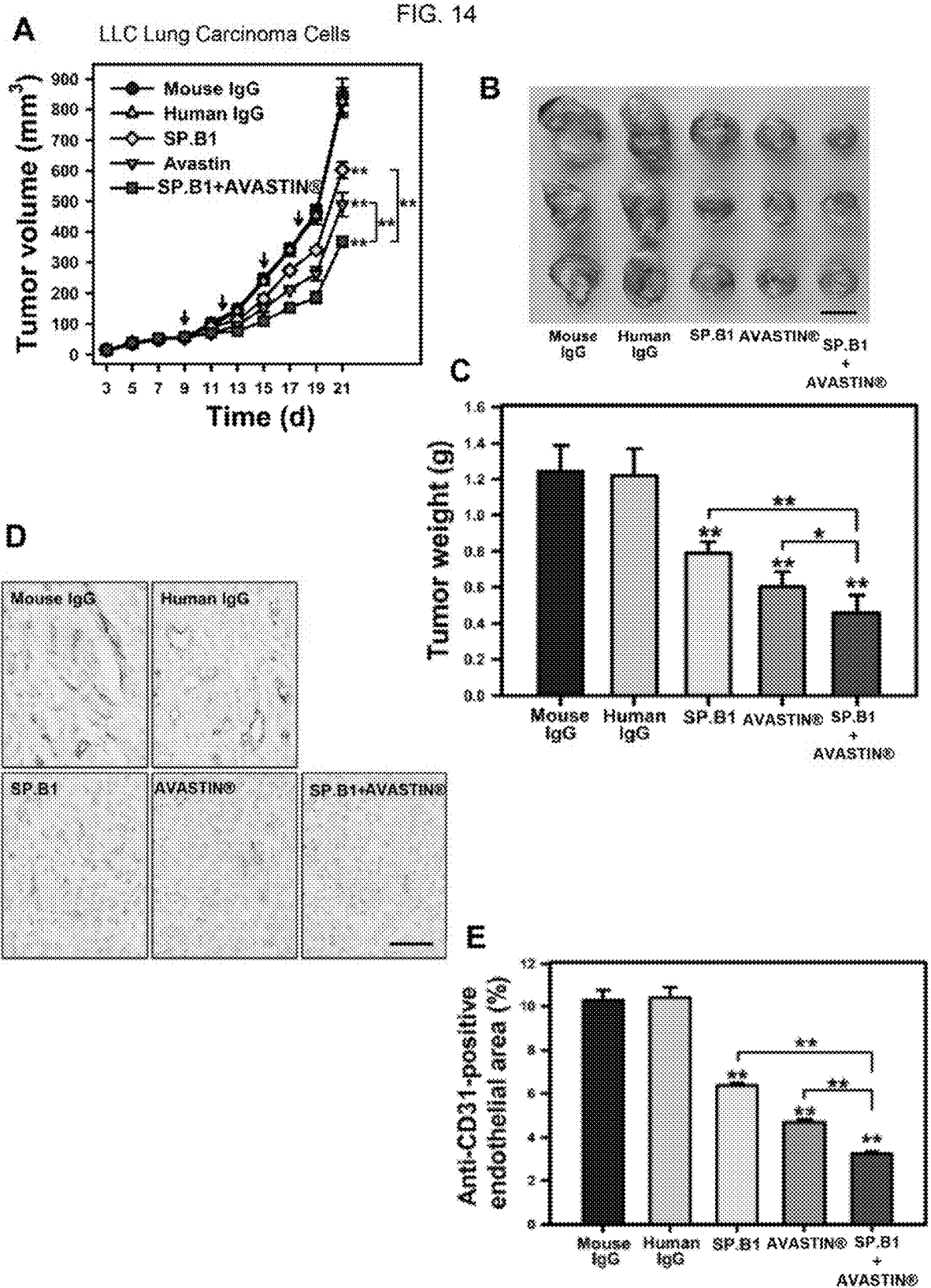
FIG. 14 shows that combined anti-SCUBE2 SP.B1 and anti-VEGF bevacizumab (AVASTIN®) treatment had an additive anti-tumor effect on lung carcinoma growth and angiogenesis. A, Mean tumor volume in each treatment group over time after injection of LLC lung carcinoma cells (n=6). Arrows indicate the times of antibody treatment. B. Representative LLC lung carcinoma in each treated xenografted mice. Scale bar:=1 cm. C, Tumors were excised and weighed (n=6/group). (D and E) Microvascular density of tumors. D and E, Representative anti-CD31 immunostaining (D) and quantified tumor vascularization (E) from lung carcinoma sections by use of IMAGEJ™. Scale bar=40 μm. *, P<0.05; **, P<0.01.

Furthermore, we established a tumor model with lung carcinoma LLC cells, which do not express SCUBE2 or VEGFR2. Incubation with SP.B1 mAb had no effect on cell growth (data not shown), so SP.B1 mAb could not target actual tumor cells, and any reduced tumor growth would result from anti-angiogenic effects. Because SCUBE2 acts as a co-receptor for VEGFR2 and bevacizumab can inhibit tumor angiogenesis, we also investigated whether combined treatment with SP.B1 and bevacizumab (AVASTIN®) could have an additive effect on suppressing lung tumor growth. Therapeutic injection was started when lung tumors reached 50 mm³. LLC growth was markedly inhibited by SP.B1, bevacizumab, and combined treatment (SP.B1+bevacizumab) as compared with mouse or human IgG treatment (FIGS. 14A-C). Furthermore. SP.B1+bevacizumab had greater inhibitory effect on tumor growth (56%) than SP.B1 (29%) or bevaciszuman (40%) alone (FIG. 14C), so these 2 agents may act at least in part on different pathways critical for tumor angiogenesis. In addition, immunohistochemical analysis showed significantly reduced microvascular density with both SP.B1 and bevacizumab treatment (FIGS. 14D-E). Importantly, vessel numbers were 49% and 31% less with SP.B1-+bevacizumab than SP.B1 and bevacizumab treatment alone, respectively. Combined treatment with SP.B1 and bevacizumab may have potential to target tumor angiogenesis in the clinic.

Figure 15:
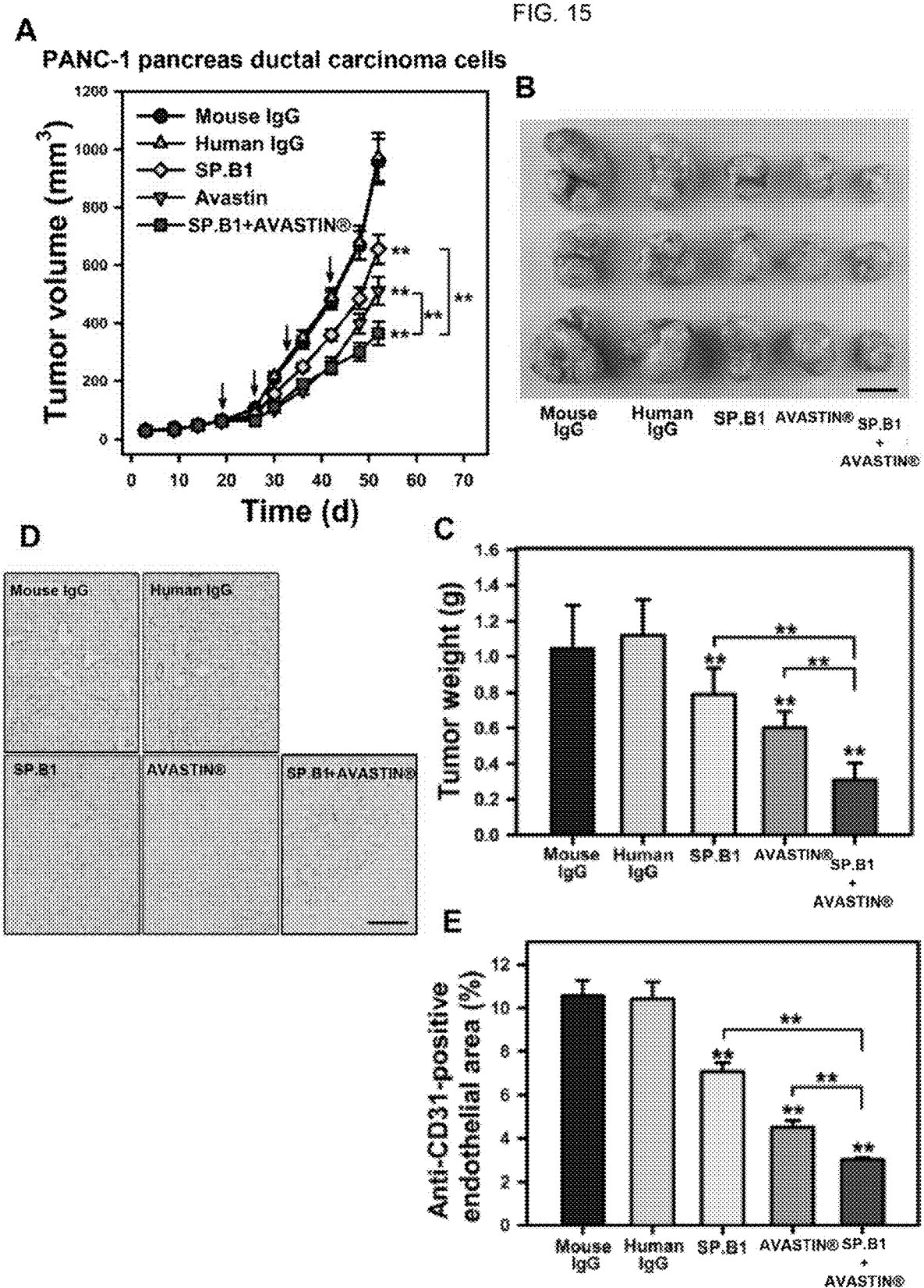
FIG. 15 shows that combined anti-SCUBE2 SP.B1 and anti-VEGF bevacizumab (AVASTIN®) treatment had an additive anti-tumor effect on pancreatic ductal carcinoma growth and angiogenesis. A, Mean tumor volume in each treatment group over time after injection of PANC-1 pancreatic ductal carcinoma cells (n=6). Arrows indicate the times of antibody treatment. B, Representative PANC-1 pancreatic carcinoma in each treated xenografted mice. Scale bar=1 cm. C, Tumors were excised and weighed (n=6/group). (D and E) Microvascular density of tumors. D and E, Representative anti-CD31 immunostaining (D) and quantified tumor vascularization (E) from pancreatic ductal carcinoma sections by use of IMAGEJ™. Scale bar=40 μm. *, P<0.05; **, P<0.01.
Figure 16:
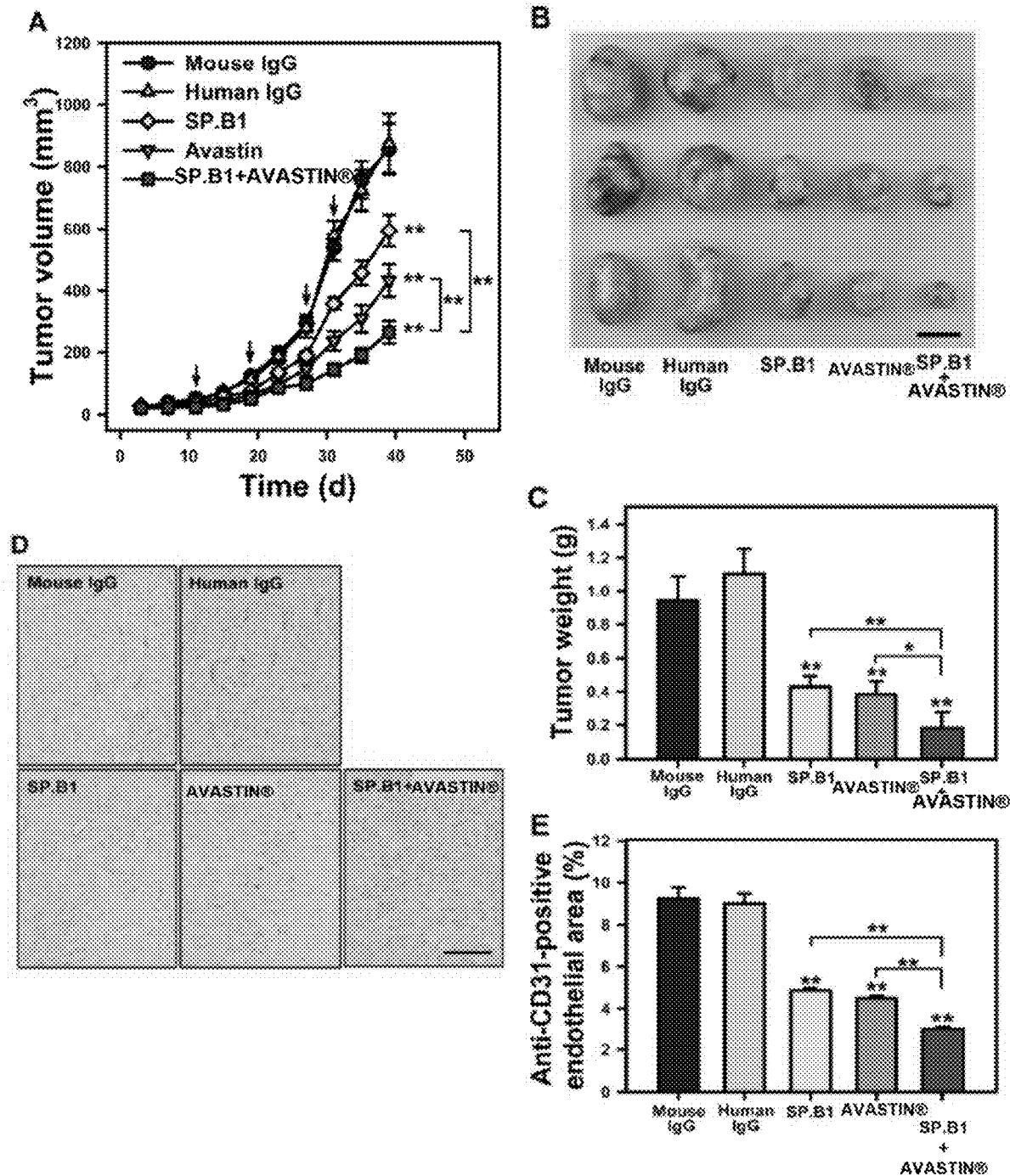
FIG. 16 shows that combined anti-SCUBE2 SP.B1 and anti-VEGF bevacizumab treatment had an additive anti-tumor effect on colorectal adenocarcinoma growth and angiogenesis. A, Mean tumor volume in each treatment group over time after injection of LS 174T colonic carcinoma cells (n=s). Arrows indicate the times of antibody treatment. B. Representative LS 174T colorectal adenocarcinoma in each treated xenografted mice. Scale bar=1 cm. C, Tumors were excised and weighed (n=6/group). (D and E) Microvascular density of tumors. D and E, Representative anti-CD31 immunostaining (D) and quantified tumor vascularization (E) from colorectal adenocarcinoma sections by use of IMAGEJ™. Scale bar=40 μm. *P<0.05: **, P<0.01.

FIG. 15 shows that combined anti-SCUBE2 SP.B1 and anti-VEGF bevacizumab (AVASTIN®) treatment had an additive anti-tumor effect on pancreatic ductal carcinoma growth and angiogenesis. FIG. 16 shows that combined anti-SCUBE2 SP.B1 and anti-VEGF bevacizumab treatment had an additive anti-tumor effect on colorectal adenocarcinoma growth and angiogenesis.

TABLE 2 mAb Clone: EGF-C3 (IgG2a)

V<sub>H</sub> domains (SEQ ID NO: 1)

| FW1 | CDR1 | FW2 | CDR2 |
|---|---|---|---|
| EVKLVESGGGLVQPGGSRKLS CVAS (SEQ ID NO: 9) | GFTISSFGMH (SEQ ID NO: 3) | WVRQAPERGLE WVA (SEQ ID NO: 10) | YISSGSNTIYYADT VKG (SEQ ID NO: 4) |

| FW3 | CDR3 | FW4 |
|---|---|---|
| RFTISRDNPKNTLFLQMTSLWS EDTAMYYCAR (SEQ ID NO: 11) | SGTLDGWFTY (SEQ ID NO: 5) | WGRGTLVTVST (SEQ ID NO: 12) |

V<sub>L</sub> domains (SEQ ID NO: 2)

| FW1 | CDR1 | FW2 | CDR2 |
|---|---|---|---|
| DIVMTQPPLSLPVSLGD QASISC (SEQ ID NO: 13) | RSSQSILHSNGNTYL E (SEQ ID NO: 6) | WYLQKPGQSPKLL IY (SEQ ID NO: 14) | KLFNRFS (SEQ ID NO: 7) |

| FW3 | CDR3 | FW4 |
|---|---|---|
| GVPDRENGSGSGTDFTL KISRAEAEDLGVYYC (SEQ ID NO: 15) | LQGSHVPPT (SEQ ID NO: 8) | FGAGTKLEIK (SEQ ID NO: 16) |

TABLE 3 mAb Clone: SP-A1 (IgG1); (same as SP-B1)

V<sub>H</sub> domains (SEQ ID NO: 17)

| FW1 | CDR1 | FW2 | CDR2 |
|---|---|---|---|
| EVQLQQSGPELVKPGAS VKVSCKAS (SEQ ID NO: 25) | GYAFTSYNMY (SEQ ID NO: 19) | WVKQSHGKSLE WIG (SEQ ID NO: 26) | YIDPYNGDTNNNQK FKG (SEQ ID NO: 20) |

| FW3 | CDR3 | FW4 |
|---|---|---|
| KATLIVDKSSSTAYMH LNSLTSEDSAVYYCAR (SEQ ID NO: 27) | SYRYLAWFAY (SEQ ID NO: 21) | WGQGTLVTVSA (SEQ ID NO: 28) |

V<sub>L</sub> domains (SEQ ID NO: 18)

| FW1 | CDR1 | FW2 | CDR2 |
|---|---|---|---|
| DIVMTQSPLSLPVSLGD QASISC (SEQ ID NO: 29) | RSSQSIVHSNGNTYL E (SEQ ID NO: 22) | WYLQKPGQSPKLLIY (SEQ ID NO: 30) | TVSNRFS (SEQ ID NO: 23) |

| FW3 | CDR3 | FW4 |
|---|---|---|
| GVPDRFSGSGSGTDFTL RISRVEAEDLGVYYC (SEQ ID NO: 31) | FQGSHIPYT (SEQ ID NO: 24) | FGGGTKLELK (SEQ ID NO: 32) |

TABLE 4 mAb Clone: SP-B1 (IgG1)

V<sub>H</sub> domains (SEQ ID NO: 17)

| FW1 | CDR1 | FW2 | CDR2 |
|---|---|---|---|
| EVQLQQSGPELVKPGAS VKVSCKAS (SEQ ID NO: 25) | GYAFTSYNMY (SEQ ID NO: 19) | WVKQSHGKSLE WIG (SEQ ID NO: 26) | YIDPYNGDTNNNQK FKG (SEQ ID NO: 20) |

TABLE 4-continued mAb Clone: SP-B1 (IgG1)

| FW3 | CDR3 | FW4 |
|---|---|---|
| KATLTVDKSSSTAYMH LNSLTSEDSAVYYCAR (SEQ ID NO: 27) | SYRYLAWFAY (SEQ ID NO: 21) | WGQGTLVTVSA (SEQ ID NO: 28) |

V_L domains (SEQ ID NO: 18)

| FW1 | CDR1 | FW2 | CDR2 |
|---|---|---|---|
| DIVMTQSPLSLPVSLGD QASISC (SEQ ID NO: 29) | RSSQSIVHSNGNTYL E (SEQ ID NO: 22) | WYLQKPGQSPKL LIY (SEQ ID NO: 30) | TVSNRFS (SEQ ID NO: 23) |

| FW3 | CDR3 | FW4 |
|---|---|---|
| GVPDRFSGSGSGTDFTL RISRVEAEDLGVYYC (SEQ ID NO: 31) | FQGSHIPYT (SEQ ID NO: 24) | FGGGTKLELK (SEQ ID NO: 32) |

TABLE 5 mAb Clone: SP-B2 (IgG1)

V_H domains (SEQ ID NO: 33)

| FW1 | CDR1 | FW2 | CDR2 |
|---|---|---|---|
| EVQRVESGGGLVKPGG SLKLSCAAS (SEQ ID NO: 41) | GFTFRNYAMS (SEQ ID NO: 35) | WVRQTTEKKLE WVA (SEQ ID NO: 42) | TINDVGSYTYFPASV KG (SEQ ID NO: 36) |

| FW3 | CDR3 | FW4 |
|---|---|---|
| RFTVSRDNTKNTLYLQ MSSLRSEDTAMYYCVT (SEQ ID NO: 43) | SSDTVPHHHALDY (SEQ ID NO: 37) | WGQGSSVTVSS (SEQ ID NO: 44) |

V_L domains (SEQ ID NO: 34)

| FW1 | CDR1 | FW2 | CDR2 |
|---|---|---|---|
| DIVMTQPPASLAVSLGQ RATVFC (SEQ ID NO: 45) | RASQNVDSRGISFMH (SEQ ID NO: 38) | WYQQKPGQPPKL LIY (SEQ ID NO: 46) | AASNLES (SEQ ID NO: 39) |

| FW3 | CDR3 | FW4 |
|---|---|---|
| GIPARFRGSGSGTDFTL NIHPVEEEDVATYYC (SEQ ID NO: 47) | QQSVEDLT (SEQ ID NO: 40) | FGGGTKLELK (SEQ ID NO: 48) |

TABLE 6 mAb Clone: CR-#5 (IgG2b)

V_H domains (SEQ ID NO: 49)

| FW1 | CDR1 | FW2 | CDR2 |
|---|---|---|---|
| EVQRVESGGDLVKPGG TLKLSCAAS (SEQ ID NO: 57) | GFTFRNYGMS (SEQ ID NO: 51) | WVRQTPDKRLE WVA (SEQ ID NO: 58) | TISSGGVYTYYPDSV KG (SEQ ID NO: 52) |

TABLE 6-continued

| mAb Clone: CR-#5 (IgG2b) | | |
|---|---|---|
| FW3 | CDR3 | FW4 |
| RFTISRDNAKNTLFLQM SSLRSEDSAMYYC (SEQ ID NO: 59) | ARDDYDGRGYFDY (SEQ ID NO: 53) | WGQGTTLIVSS (SEQ ID NO: 60) |

| $V_L$ domains (SEQ ID NO: 50) | | | |
|---|---|---|---|
| FW1 | CDR1 | FW2 | CDR2 |
| DIVMSQSPSSLAVSAGE KVTMSC (SEQ ID NO: 61) | KSSQSLLNSRTRKNY LA (SEQ ID NO: 54) | WYQQKPGQSPKL LIY (SEQ ID NO: 62) | WASTRES (SEQ ID NO: 55) |
| FW3 | CDR3 | FW4 | |
| GVPDRFTGSGSGTDFTL TISSVQAEDLAVYYC (SEQ ID NO: 63) | KQSYNLPT (SEQ ID NO: 56) | FGSGTKLDIK (SEQ ID NO: 64) | |

In summary, we showed that SCUBE2 but not SCUBE1 or 3 was specifically upregulated by HIF-1α in HUVECs under hypoxia. This unique hypoxic induction of SCUBE2 might explain in part its distinctive role in regulating blood flow recovery after hind-limb ischemia. The involvement of SCUBE2 in angiogenesis was not restricted to the action of VEGF. Further studies are needed to clarify whether SCUBE2 participates in postnatal angiogenesis mediated by sonic hedgehog or VE-cadherin signaling. Here, our data revealed SCUBE2 as a novel VEGFR2 co-receptor that regulates VEGF-induced tube formation and proliferation of ECs by fine-tuning VEGFR2-mediated signaling. SCUBE2 may have clinical importance in the pathogenesis of various angiogenesis-related diseases such as atherosclerosis, diabetic retinopathy, and age-related macular degeneration. In addition to its expression in normal organ ECs, SCUBE2 is also highly expressed in the ECs of numerous types of human carcinomas and xenografted tumors (our unpublished data). Although further studies are required to validate whether endothelial SCUBE2 is involved in tumor angiogenesis, SCUBE2 may be a promising target molecule for cancer therapy because of its anti-angiogenic effect of SCUBE2 inactivation. Pharmacological blockade of endothelial SCUBE2 may represent a novel therapeutic strategy for angiogenesis-related disorders. Examples of diseases characterized or caused by abnormal or excessive angiogenesis are listed in Table 7.

TABLE 7

| Organ | Diseases |
|---|---|
| Numerous organs | Cancer (activation of oncogenes; loss of tumor suppressors); infectious diseases (pathogens express angiogenic genes, induce angiogenic programs or transform ECs); autoimmune disorders (activation of mast cells and other leukocytes) |
| Blood vessels | Vascular malformations (Tie-e mutation); DiGeorge syndrome (low VEGF and neuropilin-1 expression); HHT (mutations of endoglin or ALK-1; cavernous hemangioma (loss of Cx37 and Cx40); atherosclerosis; transplant arteriopathy. |
| Adipose tissue | Obesity (angiogenesis induced by fatty diet; weight loss by angiogenesis inhibitors) |
| Skin | Psoriasis, warts, allergic dermatitis, scar keloids, pyogenic granulomas, blistering disease, Kaposi sarcoma in AIDS patients |
| Eye | Persistent hyperplastic vitreous syndrome (loss of Ang-2 or VEGF164); diabetic retinopathy; retinopathy of prematurity; choroidal neovascularization (TIMP-3 mutation) |
| Lung | Primary pulmonary hypertension (germline BMPR-2 mutation; somatic EC mutations); asthma; nasal polyps |
| Intestines | Inflammatory bowel and periodontal disease, ascites, peritoneal adhesions |
| Reproductive system | Endometriosis, uterine bleeding, ovarian cysts, ovarian hyperstimulation |
| Bone, Joints | Arthritis, synovitis, osteomyelitis, osteophyte formation |

The foregoing description of the exemplary embodiments of the invention has been presented only for the purposes of illustration and description and is not intended to be exhaustive or to limit the invention to the precise forms disclosed. Many modifications and variations are possible in light of the above teaching. Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A monoclonal anti-signal peptide-complement protein C1r/C1s, Uegf, and Bmp1 (CUB)-epidermal growth factor (EGF) domain-containing protein 2 (SCUBE2) antibody or a binding fragment thereof, comprising an antigen binding region specifically targeting the first cysteine-rich repeat motif, the first cysteine-rich motif ranging from amino acid position 668 to 725 of SCUBE2 (SEQ ID NO: 66), the antigen binding region comprising a heavy chain variable domain ($V_H$) and a light chain variable domain ($V_L$), wherein:
   (a) the $V_H$ comprises a CDR1 comprising the amino acid sequence of SEQ ID NO: 51, a CDR2 comprising the amino acid sequence of SEQ ID NO: 52, and a CDR3 comprising the amino acid sequence of SEQ ID NO: 53; and
   (b) the $V_L$ comprises a CDR1 comprising the amino acid sequence of SEQ ID NO: 54, a CDR2 comprising the amino acid sequence of SEQ ID NO: 55, and a CDR3 comprising the amino acid sequence of SEQ ID NO: 56.

2. The monoclonal anti-SCUBE2 antibody or the binding fragment thereof of claim 1, which is humanized antibody or a chimeric antibody.

3. The monoclonal anti-SCUBE2 antibody or the binding fragment thereof of claim 1, which is selected from the group consisting of a Eli fragment, a fragment antigen-binding (Fab) fragment, a F(ab')₂ fragment, a Fab' fragment, a Fd' fragment, and a Fd fragment, and a single chain antibody variable fragment (scFv).

4. The monoclonal anti-SCUBE2 antibody or the binding fragment thereof of claim 1, which is encapsulated within a liposome.

5. A fusion protein comprising the monoclonal anti-SCUBE2 antibody or the binding fragment thereof of claim 1.

6. A method for treating a vascular endothelial growth factor (VEGF)-induced angiogenesis related disease, comprising:
   administering a therapeutically effective amount of the monoclonal anti-SCUBE2 antibody or the binding fragment thereof of claim 1 to a subject in need thereof;

wherein the VEGF-induced angiogenesis related disease is selected from the group consisting of melanoma, lung carcinoma, pancreatic carcinoma, colorectal carcinoma and retinal neovascular disease.

7. The method of claim 6, further comprising administering bevacizumab to treat the VEGF-induced angiogenesis related disease in the subject in need thereof.

8. A method for inhibiting tumor growth and tumor angiogenesis, comprising administering a therapeutically effective amount of the monoclonal anti-SCUBE2 antibody or the binding fragment thereof of claim 1 and bevacizumab to a subject in need thereof, wherein the tumor comprises SCUBE2-overexpressing vascular endothelial cells.

9. A monoclonal anti-signal peptide-complement protein C1r/C1s, Uegf, and Bmp1 (CUB)-epidermal growth factor (EGF) domain-containing protein 2 (SCUBE2) antibody or a binding fragment thereof, comprising an antigen binding region specifically targeting the first cysteine rich repeat motif, the first cysteine-rich motif ranging from amino acid position 668 to 725 of SCUBE2 (SEQ ID ID: 66), the antigen binding region comprising a heavy chain variable domain ($V_H$) and a light chain variable domain ($V_L$), wherein the $V_H$ comprises the amino acid sequence of SEQ ID NO: 49, and the $V_L$ comprises the amino acid sequence of SEQ ID NO: 50.

10. The monoclonal anti-SCUBE2 antibody or the binding fragment thereof of claim 9, which is a humanized antibody or a chimeric antibody.

11. A fusion protein comprising the monoclonal anti-SCUBE2 antibody or the binding fragment thereof of claim 9.

12. The monoclonal anti-SCURE2 antibody or the binding fragment thereof of claim 9, which is selected from the group consisting of a Fv fragment, a fragment antigen-binding (Fab) fragment, a F(ab')$_2$ fragment, a Fab' fragment, a Fd' fragment, and a Fd fragment, and a single chain antibody variable fragment (scFv).

13. The monoclonal anti-SCUBE2 antibody or the binding fragment thereof of claim 9, which is encapsulated within a liposome.

14. A method for treating a vascular endothelial growth factor (VEGF)-induced angiogenesis related disease, comprising:
   administering a therapeutically effective amount of the monoclonal anti-SCUBE2 antibody or the binding fragment thereof of claim 9 and bevacizumab to a subject in need thereof;
   wherein the VEGF-induced angiogenesis related disease is selected from the group consisting of melanoma, lung carcinoma, pancreatic carcinoma, colorectal carcinoma and retinal neovascular disease.

15. A method for inhibiting tumor growth and tumor angiogenesis, comprising administering a therapeutically effective amount of the monoclonal anti-SCUBE2 antibody or the binding fragment thereof of claim 9 and bevacizumab to a subject in need thereof, wherein the tumor comprises SCUBE2-overexpressing vascular endothelial cells.

16. A fusion protein comprising a heavy chain variable domain ($V_H$) and a light chain variable domain ($V_L$), wherein:
   the $V_H$ comprises the amino acid sequence of SEQ ID NO: 49, and the $V_L$ comprises the amino acid sequence of SEQ ID NO: 50; and further wherein:
   the fusion protein comprises an antigen binding region specifically targeting the first cysteine-rich repeat motif, the first cysteine-rich motif ranging from amino acid position 668 to 725 of SCUBE2 (SEQ ID NO: 66).

17. The fusion protein of claim 16, which is a single chain antibody variable fragment (scFv).

* * * * *